(12) United States Patent
Abouelsoud

(10) Patent No.: US 11,654,281 B2
(45) Date of Patent: May 23, 2023

(54) NEURAL STIMULATION DEVICE

(71) Applicant: U, LLC, Mayfied Heights, OH (US)

(72) Inventor: Mohammed Abouelsoud, Mayfield Heights, OH (US)

(73) Assignee: U, LLC, Columbus, OH (US)

( * ) Notice: Subject to any disclaimer, the term of this patent is extended or adjusted under 35 U.S.C. 154(b) by 0 days.

(21) Appl. No.: 17/336,224

(22) Filed: Jun. 1, 2021

(65) Prior Publication Data
US 2021/0370063 A1    Dec. 2, 2021

Related U.S. Application Data

(60) Provisional application No. 63/032,332, filed on May 29, 2020.

(51) Int. Cl.
*A61N 1/36* (2006.01)
*A61N 1/04* (2006.01)

(52) U.S. Cl.
CPC ....... *A61N 1/36025* (2013.01); *A61N 1/0456* (2013.01); *A61N 1/0476* (2013.01); *A61N 1/36031* (2017.08); *A61N 1/36034* (2017.08)

(58) Field of Classification Search
CPC ............ A61N 1/36031; A61N 1/36034; A61N 1/36025; A61N 1/0456; A61N 1/0476
See application file for complete search history.

(56) References Cited

U.S. PATENT DOCUMENTS 9,662,492 B1 * 5/2017 Tucker .................. A61N 2/002

\* cited by examiner

*Primary Examiner* — Alyssa M Alter
(74) *Attorney, Agent, or Firm* — Troutman Pepper Hamilton Sanders LLP

(57) ABSTRACT

Neurostimulation devices and methods provide a plurality of electrodes placed around a patient head such that electrode have electrical paths through the brain to other electrodes. A controller controls current between sets of opposing electrodes through the patient brain to selectively stimulate a region of interest of the patient brain. Different sets of electrodes are used to provide electrical current pulse with different polarities such that a net potential is exposed to a region of interest in the brain that it above a neuron stimulation threshold while a net potential exposed to tissue outside the region of interest is below the threshold.

20 Claims, 23 Drawing Sheets

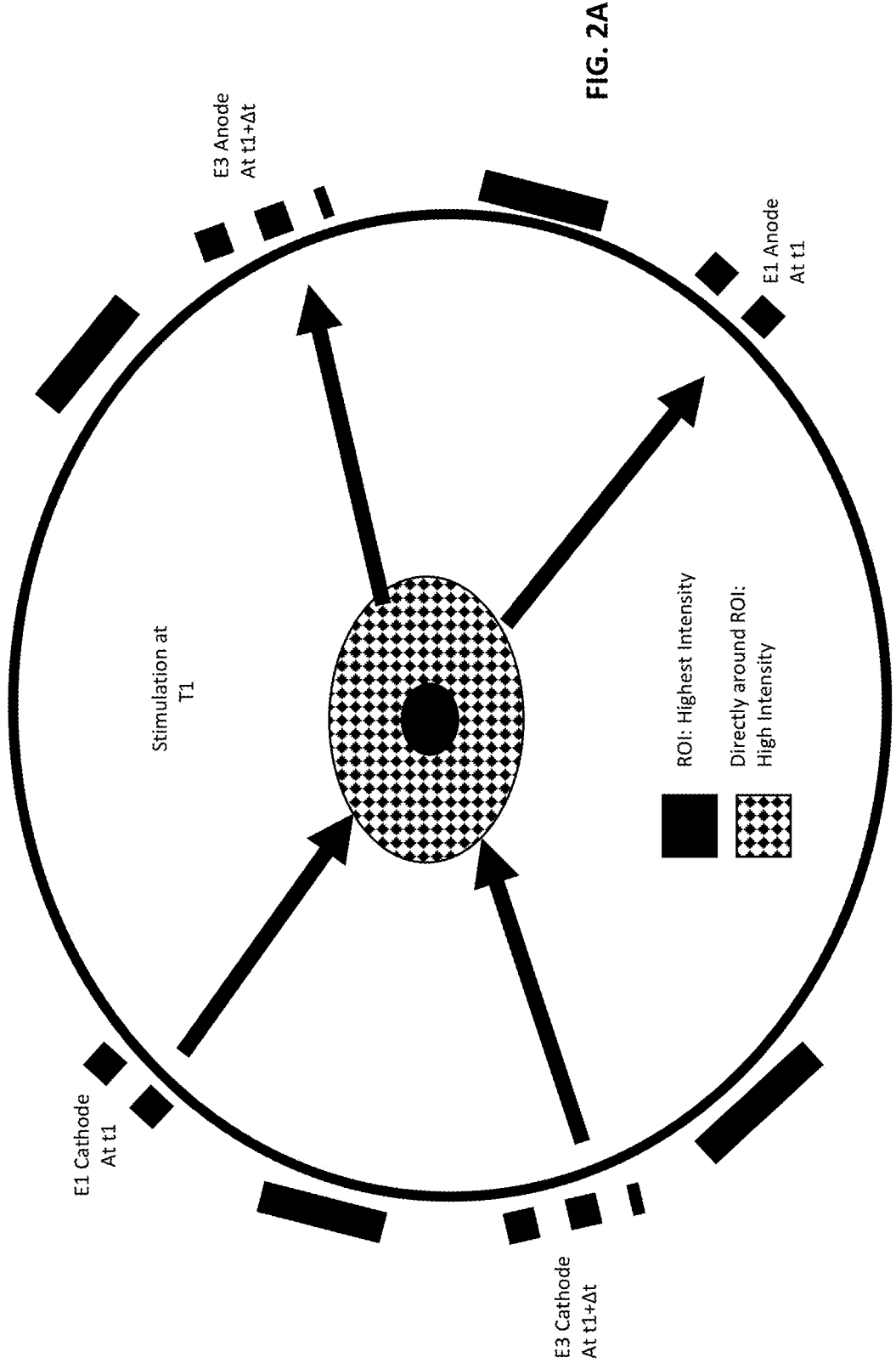

T0

T1

T2, T2 + Δt

T3, T3 + Δt $\Theta_1 = \tan^{-1}(sL/nd)$ and $\Theta_2 = \pi/2 - \Theta_1$ $d/2 * (sL/nd) = sL/2n = z$ $h = L - sL/n = L(1 - s/n)$ $w = h(sL/nd) = d(n-s)/s$

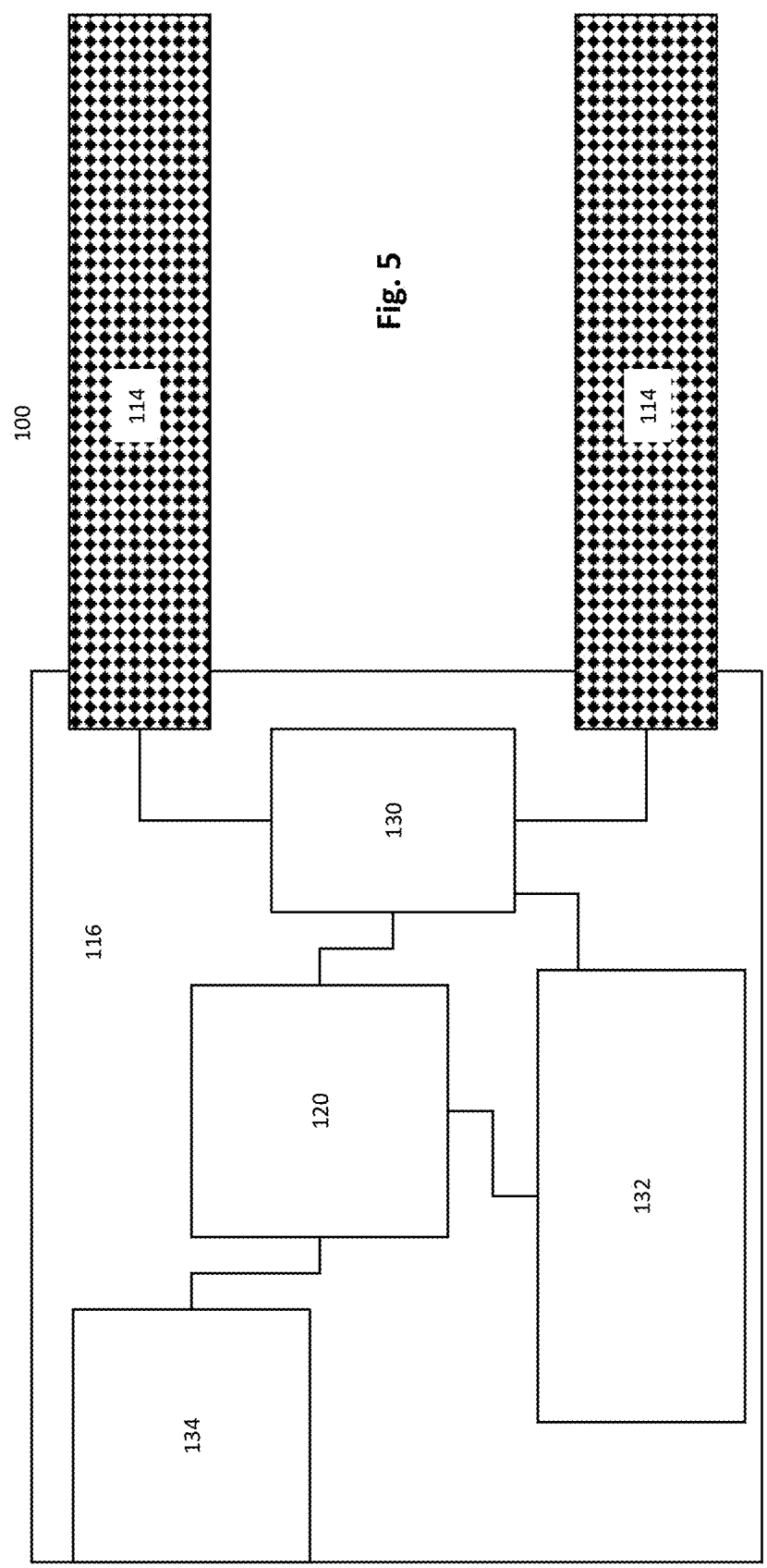

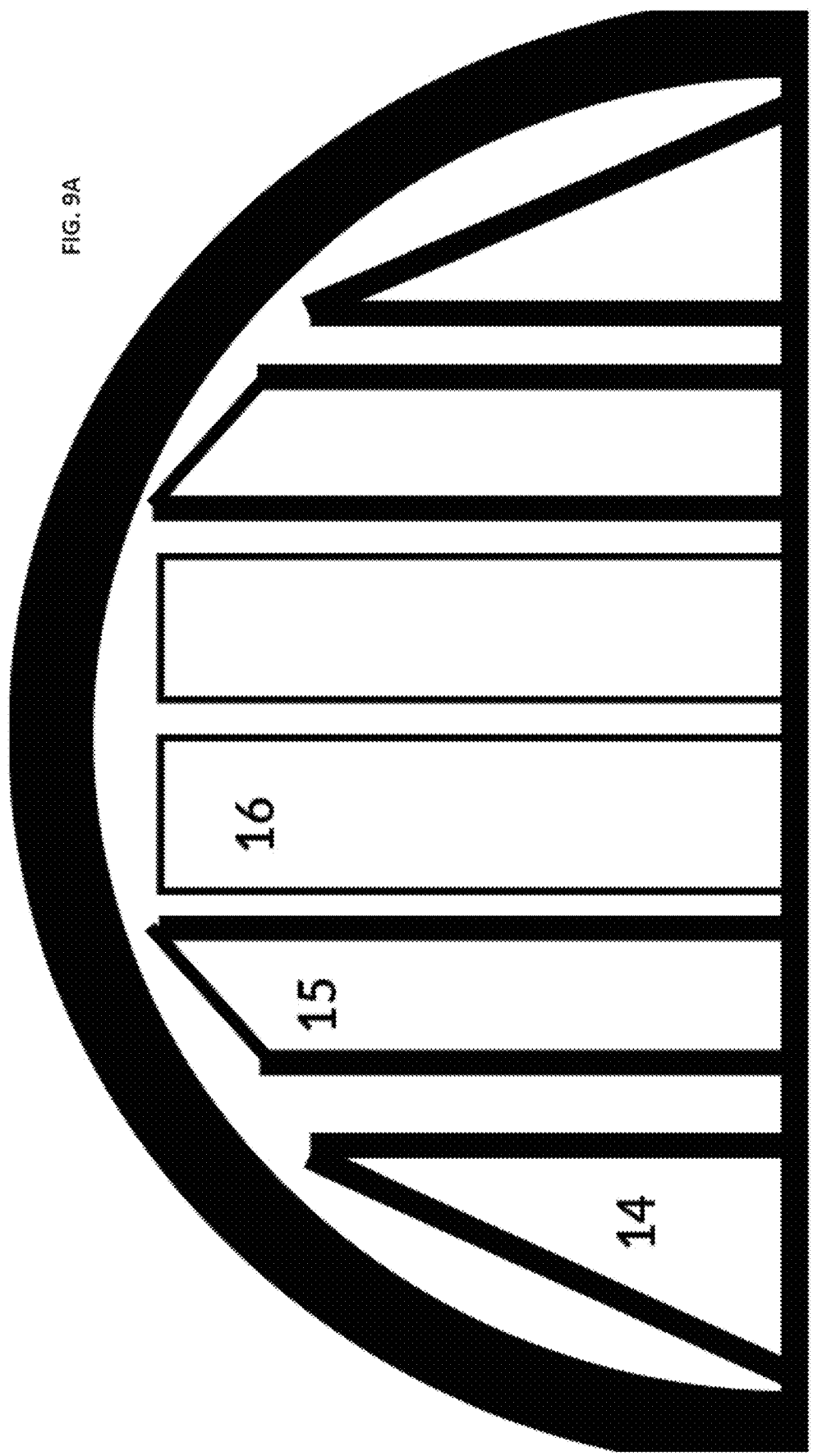

NEURAL STIMULATION DEVICE

CROSS-REFERENCE TO RELATED APPLICATIONS

This application claims the benefit of U.S. Provisional Application Ser. No. 63/032,332 filed May 29, 2020, which is incorporated herein by reference in its entirety.

TECHNICAL FIELD

The present disclosure relates generally to methods, systems, and apparatuses related to a neurostimulation system that includes various hardware and software components that work together to provide targeted stimulation of patient tissue. The disclosed techniques may be applied to, for example, treatment of various neurological disorders such as Parkinson's Disease, essential tremor, different classes of multiple sclerosis, major depressive disorder, bipolar disorder type I/II, dementia of the Alzheimer's type (DAT), traumatic brain injury, generalized anxiety disorder, different classes of mild cognitive impairment, drug-resistant epileptic disorders, ADHD and ADD, and different classes of stroke.

BACKGROUND

Neuromodulation is defined as the use of a targeted stimulation to alter nerve activity at specific neurological sites in the body. There are 6 major classes of neuromodulation: electrical, magnetic, optogenetics, thermal, Acoustic/Mechanical, and Chemical. The safety of a modulation method is of the primary importance.

Neural-Stimulation using electrical stimulation is a neuromodulation therapy for the treatments of many neuropsychiatric disorders such as Parkinson's Disease, essential tremor, different classes of multiple sclerosis, major depressive disorder, bipolar disorder type I/II, dementia of the Alzheimer's type (DAT), traumatic brain injury, generalized anxiety disorder, different classes of mild cognitive impairment, drug-resistant epileptic disorders, ADHD and ADD, and different classes of stroke. All classes of neuropsychiatric disorders have distinct functional and structural connectivity. There is extensive literature showing alterations in both functional and structural connectivity after neural-stimulation protocols. Thus, having the ability to alter functional and structural connectivity in the human cortex can alter the disease state in a neuropsychiatric disorder. This is one of the basic principles of neural-stimulation being used in the treatment, mitigation, or prevention of neuropsychiatric disorders as well as the main mechanism of action from the new neuromodulation techniques described in the claims below.

Neural-Stimulation takes form in both invasive and non-invasive procedures. Patients that do not respond to pharmacotherapy or psychotherapy like SSRIs/Therapy are candidates for neuromodulation procedures such as transcranial magnetic stimulation (TMS), transcranial current stimulation (TCS), and electroshock therapy (ECT). ECT is an extremely effective therapy for treatment resistant depression where electrodes induce brief seizures with electrical current into the brain. However, traditional ECT comes with dangerous side effects such as migraines, anterograde and retrograde amnesia, cognitive dysfunction, memory loss, and delirium. While ECT has fewer side effects, the cost, efficacy, mobility, and timeliness of the treatment can be improved. TMS is an often ineffective technique, relying on large magnetic fields to induce electrical current in superficial regions of the brain. TCS delivers weak electrical currents to the brain via electrodes to prime underlying regions. While safe, at low currents, TCS is incapable of inducing neurophysiological effects and at high currents, TCS can lead to skin damage, phosphenes, or headaches. Noninvasive neuromodulation therapies could benefit from improvements to the focality of stimulation, precision of stimulated regions, the depth of the stimulation site, and personalize the treatment for the patient.

Key brain regions such as the human reward system lie deep within the brain, generally beyond the extent of most current noninvasive techniques. These deep brain regions are the anterior thalamic nucleus, entorhinal cortex, central thalamus, inferior thalamic peduncle, fornix and superior lateral branch of the medial forebrain bundle. As these regions lie deep within the cortex, attempting to activate them with current stimulation methods is generally ineffective. Invasive treatments like deep brain stimulation (DBS) can address these regions. DBS provides a focused and clinically effective approach to the treatment of neuropsychiatric with some degree of targeting the various structures of interest for stimulation. In spite of its effectiveness, the labor, risks, invasiveness and time of surgery renders DBS as a last resort, non-scalable treatment that very few patients can afford financially and medically. DBS can induce neurogenesis in mice brains. Neurogenesis is the process where neurons are produced in certain regions of the brain, specifically in the subgranular zone of the dentate gyrus in the hippocampus, a region that is critical in regulating learning, memory, and emotions. When neurogenesis is induced in mice, the mice exhibit an alleviation of symptoms that is measured through various protocols such as the tail suspension test, and the elevated plus maze. When DBS, or electromagnetic radiation from ECT, is used on certain regions of the brain, neurogenesis can increase beyond the base proliferation rate. DBS stimulation trials have been on the superior lateral branch of the medial forebrain bundle (slMFB). Acute antidepressant effects were reported during intraoperative stimulation of the slMFB showing high rationale that stimulation of the human reward system is a worthwhile region of interest in the treatment of neuropsychiatric disorder. However, since the slMFB is an area deep in the human reward system, surgery does not seem to be a cost effective, scalable, and expedited process for neuropsychiatric disorder treatment.

Studies have shown various potential benefits to DBS, including neurogenesis, reduced depression scores on the Hamiltonian scale, antidepressant effects with minimal relapse, reduction of seizure in epileptic patients, reduction in compulsive thoughts, increased attention/memory, and measurable increases in IQ. However, traditional DBS techniques are highly invasive. DBS also shows favorable effects for other neuropsychiatric diseases including, but not limited to: Parkinson's disease, epilepsy, Alzheimer's disease, OCD, PTSD, and essential tremor. It is desirable to devise a non-invasive technique that achieves some or all of these benefits.

There are key biomarkers in the cortex that can be modulated through noninvasive neuromodulation. Widespread structural abnormalities have been reported including regional tissue loss in the hippocampus, amygdala, basal ganglia, prefrontal cortex, and anterior cingulate cortex. These results suggested that a dysfunctional cortical-sub-cortical neural circuit is involved in the pathophysiology and psychopathology of neuropsychiatric disorders. Investigations of white matter have become a rapidly growing interest in the investigation of mood or affective disorders. Reduced white matter fractional anisotropy was measured in the genus of the corpus callosum. The corpus callosum (CC) is the largest white matter tract that connects the two hemispheres of the brain together and the genus of the CC is contained in the rostral region, near to the prefrontal cortex. Patients with a disruption in axonal myelination exhibit executive deficits as well as cognitive dysfunction.

Neuropsychiatric diseases and abnormalities also have an influence on electroencephalogram (EEG) oscillatory behaviors. EEG provides brain activity on fast, millisecond time scales which is strongly influenced by white matter axons. There are many computer methods to provide models of the brain's surface at roughly the 2-3 cm scale. The relationships between gray and white matter structure and connectivity are responsible for the dynamic behavior of the brain and recording measurements made with EEG; any impairment made to this complex system as a result of a neurological disorder can be elucidated from EEG measurements. There is an important relationship between alpha and theta bands and axon propagation. Myelinated axons (white matter) control action potential speed and the synchrony of long distant regions which is important in maintaining the stability of executive functions including mental performance, learning, memory acquisition and recall, and mood regulation. A broad range of psychiatric disorders, including schizophrenia, chronic depression, bipolar disorder, obsessive-compulsive disorder, and posttraumatic stress disorder, has recently been associated with white matter defects, as have neurodevelopmental cognitive and emotional disorders including autism, dyslexia and attention-deficit hyperactivity disorder.

Intersectional Short Pulse stimulation technique (ISP) has shown some success with neurogenesis. ISP utilizes multiple electrode pairs with current distributed among them while temporally multiplexing between which pair is active at any time. The theory behind ISP is that crossover of fields creates a strong pocket deep in the brain. However, ISP fails to control the geometry of the pocket in the brain. Multiple electrodes can help focus stimulation, causing less skin burning, and minimal headache. For example, in WO 2018/213622 A1 (Berenyi, et al.), monophasic pulses multiplexed through four electrode pairs interleave ISP stimulation epochs, where the adjacent electrode pairs are stimulated with opposite polarity. This creates a shuffled ISP effect, where the alternating direction of the injected electric fields from shuffled firing of ISP electrodes pairs causes a summed effect in neurons that should be close to zero for much of the volume of the brain. However, the technique disclosed therein does not do a great job of targeting small regions of the brain in a non-invasive manner. Furthermore, the technique can cause undesirable side effects including metallic tasting, intense burning on skin, and changes in the visual field of the subject. Furthermore, ISP stimulation has not been used for specific diseases and the stimulation still targets surrounding regions of the brain. Methods and systems outlined below can overcome one or more of these problems.

Temporal Interference (TI) is another advanced neuromodulation method that emerged from Ed Boyden's lab in 2017 from MIT. This method of stimulation uses multiple high-frequency electric fields that interfere in deep regions of the brain without stimulating other areas. The problem with TI is the scattering of electrodes across the entire skull and the inability to localize the field as well as other techniques. Furthermore, TI fails to carve out specific geometric fields in the brain using a plurality of electrodes and sub-electrodes and also does not create a specific pulse protocol outlined for each type of neurodegenerative disease. As seen in, WO 2016/057855 A1 (Grossman, et al.), TI needs to place electrodes all around the brain to target deep regions of the cortex. TI does not utilize downstream action potential elications to active deep regions of the cortex.

Another major shortcoming in the neuromodulation community is the short time frame treatments. With the exception of implantable neuromodulation units, treatments are usually done for a maximum of 8 weeks. For example, Transcranial Magnetic Stimulation is a 1 hour noninvasive treatment procedure that patients have to drive to a hospital or private clinic to utilize. A trained research technician needs to set up the TMS equipment and administer the pulses. The procedure costs around $300 a session and lasts up to 6 weeks. This is not highly beneficial for treatment resistant patients who need a higher number of sessions to see results on their disease. Having a portable and cost-effective technology and method that can send pulses into the cortex for greater than 8 weeks could be useful in the neuromodulation community that will revolutionize the neuromodulation industry and the entire healthcare system.

SUMMARY

Embodiments of the present invention address and overcome one or more of the above shortcomings and drawbacks by providing targeted electrical pulses from offset electrode to stimulate a region of interest in the brain while minimizing net current and voltage in other regions of the brain and scalp.

According to some embodiments, a neurostimulation device includes a plurality of electrodes configured to be placed around at least a portion of a patient head such that each electrode has a plurality of electrical paths through the brain of the patient to at least a subset of the other electrodes. The device further includes a controller configured to selectively control current between sets of opposing electrodes through the patient brain to selectively stimulate a region of interest of the patient brain. This can be accomplished by providing a first set of electrical current pulses across the region of interest using a first set of opposing electrodes and providing second and third sets of electrical current pulses across the region of interest using a second and third set of opposing electrodes, each offset from the first set of electrodes. The second set of electrical current pulses is of a substantially opposite polarity to the first and third sets of electrical current pulses, and a first net potential exposed to the region of interest by first, second, and third sets of electrical current pulses exceeds a neuron stimulation threshold and a second net potential exposed to areas of the patient brain outside the region of interest is less that the neuron stimulation threshold. In some embodiments, rather than second and third sets of pulses are provided outside the region of interest, rather than through that region to limit the net electrical stimulation outside that region.

According to one aspect of some embodiments, the first net potential can have a voltage gradient in the region of interest that does not exceed 10 mV/mm (more than 1 mV/mm is a rough minimum activation threshold in many embodiments) and a current through the patient's scalp provided by the electrodes does not exceed 4 mA. According to another aspect, each electrode can include an array of sub electrodes. Further, the controller can be configured to selectively operate subsets of sub electrodes within the arrays to form the sets of opposing electrodes. The controller can also be configured to repeatedly provide cycles of the first second and third sets of electrical current pulses at a rate of 10 Hz-100 kHz for a predetermined time. The controller can also be configured to vary the subsets of sub electrodes selected during the predetermined time.

According to other aspects of some embodiments, electrodes can be configured and used as EEG sensors for the controller. The controller can also be configured to modify electrical pulse parameters of at least one of the first, second, and third sets of electrical current pulses based on information gathered from the sensors. Pulse waveform sequences can be generated by an alternating current, direct current, or modified alternating current. Pulse waveforms sequences can be modulated via pulse polarity, amplitude, wavelength, pulse shape, and inter-pulse duration. Pulse modulation can be induced via a ground-independent switching circuit coded to generate electric field gradients with various properties.

In some embodiments, a neurostimulation method for stimulating a region of a patient brain includes placing a plurality of electrodes around at least a portion of a patient head such that each electrode has a plurality of electrical paths through the brain of the patient to at least a subset of the other electrodes, wherein the electrodes are energized under control of a controller. The method can include providing a first set of electrical current pulse across the region of interest using a first set of opposing electrodes and providing second and third set of electrical current pulses across a portion of the patient brain using a second and third set of opposing electrodes, each offset from the first set of electrodes. The second set of electrical current pulses is of a substantially opposite polarity to the first and third sets of electrical currents, and the controller selects the first, second, and third electrical currents such that a first net potential exposed to the region of interest exceeds a neuron stimulation threshold and a second net potential exposed to areas of the patient brain outside the region of interest is less that the neuron stimulation threshold.

According to other aspects of some embodiments, a network of electrodes, sub-electrode groups, and sub-electrode networks can exhibit one or more possible pulse waveforms at a single point in time. Each pulse waveform from the diverse array of electrodes and sub-electrodes can have its own specific properties. A cycle of pulses to produce electric field gradients can include activation and deactivation of pulse waveforms with many possible waveforms properties per cycle. Possible DC duty-cycles can range from 0% to 100% to elicit different neuronal spike train firing frequencies. Pulse waveforms can exhibit one or more duty-cycles per a given period of time. Pulse waveforms can exhibit one or more frequency of pulses per given period of time with a frequency range of 0 Hz to 100,000 Hz. pulse waveforms can exhibit one or more amplitude per given period of time ranging from 0 to 8 mA current output. Pulse waveforms can exhibit different monophasic or biphasic shapes of pulses, as such different polarity of electric field gradients in the brain. Pulse waveforms can exhibit one or more length of pulses per given period of time. Pulse waveforms can exhibit one or more intra-pulse durations per given period of time. Pulse waveforms can be an Alternating Current, Direct Current, or Modified Alternating Current per given period of time. Pulse waveforms can produce electric field gradients along the forceps minor, corticospinal tracts, regions in the frontal cortex, anterior thalamic radiating bundles, and fibers along the corpus callosum. Any or all of these can be selected based on a treatment plan created by patient data and feedback during treatment.

In some embodiments, each electrode can have sub-electrodes and each sub-electrode can operate with other sub-electrodes in a sub-electrode group. Sub-Electrode groups can operate with one or more sub-electrode groups in a sub-electrode group network. Multiple sub-electrode group networks can be on simultaneously to cross fire onto a region of interest or fired one at a time in rapid succession. Computational head models can be used to calculate optimal sub-electrode networks parameters to target region of interest(s). A single sub-electrode network can change in real-time while device is on to evolve into a different sub-electrode network (which can be referred to as sub-electrode network dynamics). Sub-electrode network dynamics can be calculated to further optimize resolution of stimulation on region of interest(s) and definition of cancelation outside of the region of interest(s). Sub-electrode network dynamics can have parameters independent of pulse parameters, which can include: length of time on/off; sequence in the stimulation protocol; the number sub-electrode groups in the network; the specific sub-electrodes groups; and inter-sub-electrode network relationships each with independent parameters. Pulse parameters emerging from electrodes can include: pulse-length; interpulse-width; current amplitude; length of time on; frequency of pulses; polarity of pulses; and shape of pulses. Sub-electrode network and pulse parameters can be modified from neural signal voltage potential derived from EEG via machine learning.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 2A-2D is a representation of an exemplary firing pattern for subsets of electrodes in each bilateral array for use with some embodiments;

FIG. 5 is a system diagram of a neural stimulation headset for use with some embodiments;

DETAILED DESCRIPTION OF EMBODIMENTS

Figure 1A:
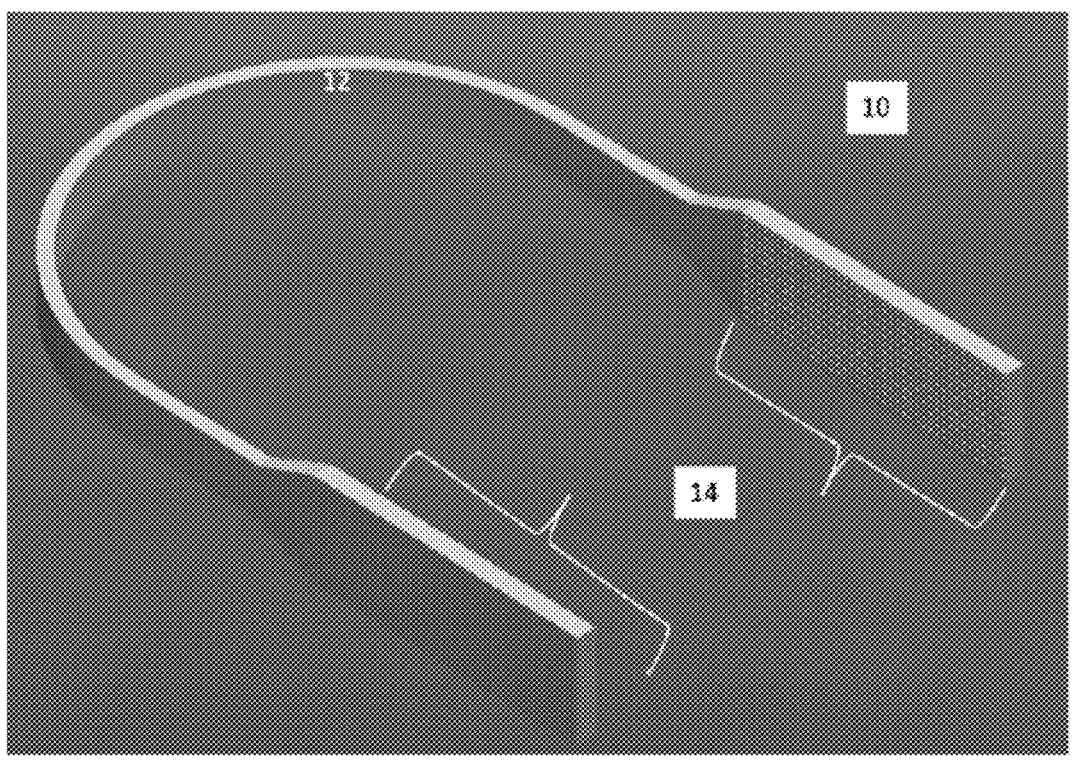
FIG. 1A is a perspective view of a wearable electrical stimulation device for use with some embodiments.

One or more pairs of arrays of electrodes are arranged on a headpiece or band, galvanically isolated and driven by a driver circuit under microcontroller control. The array pair(s) are arranged to be placed on the head of a patient, spaced laterally, on opposite sides of the head. The electrodes are configured to use transcutaneous electrical pulses between a pair of bilateral electrode groups to stimulate structures in the thalamus and parahippocampal gyri. In some embodiments, a scattered electrode frame that optimizes current flow through the device reduces skin sensation and distributes current across several smaller, densely spaced electrodes. This allows for a compact distribution of electrodes on the head to reduce irritation and distribute current.

Multiplexing occurs quickly with multiple electrodes. This allows the area in the brain where the electric field gradient lines converge to have a larger voltage gradient when compared to just one electrode pair without over stimulating the skin surface. The speed of the multiplexing cycle exploits the time-integrity constraint of neurons. This circumvents current injection problems that can lead to pain, and facilitates focality/current magnitude of stimulation on deep regions of the brain, which has hindered the other noninvasive techniques in the art. Embodiments use a new stimulation paradigm that further improves the focality of stimulation deep within the brain, while also allowing the multiple electrode pairs to stay close together. This improves the treatments available for neuropsychiatric disorders, as the device can be compact and comfortable, cost effective, and lightweight. The stimulation paradigm stimulates the thalamic region of the brain to induce neurogenesis. Specifically, in some embodiments, monophasic and biphasic current waveforms are applied through multiple electrode groups. This deviates from prior art ISP stimulation techniques that strictly uses a monophasic waveform. Monophasic pulses are pulses of current through a medium that has a single phase and, therefore, polarity over time. Biphasic pulses are pulses of current through a medium that has two phases, and therefore, two opposite polarities over time.

By using charged biphasic waveforms (stimulating with opposite polarity) with a delay, efficacy problems associated with simple cancellation of charging effect from the polarity reversal can be mitigated. The delay allows other electrodes to fire monophasic pulses, increasing the stimulation focality of the area of interest over time, and reduces the amount of electrode pairs needed. This approach can be described as Multiplicative Increase Additive Decrease (MIAD) stimulation.

Prior art ISP stimulation distributes currents through multiple electrodes by temporal multiplexing, i.e., rapidly switching currents between multiple electrode pairs faster than the time integrity constant of neurons onto a singular point of interest in the brain. This spreads out current on the scalp and minimizes skin sensation. By rapidly switching between electrodes firing, one can induce a larger field potential in the region of the brain where the electric field gradient of the switching electrodes converge upon. MIAD is similar to this approach, increasing the focality of the stimulation over time while also using fewer electrodes onto a large region of interest in the brain. MIAD creates symmetric distributions of charge in regions that we do not want stimulated and asymmetric distributions in the regions that we want to depolarize for the therapeutic effect. Targeting the thalamus and its substructures can help alleviate depressive symptoms and support cognition in individuals.

Any electrical current applied to a neuron will modify the voltage levels around the neuron. The modified voltage levels affect the lengths in which the voltage-gated sodium channels are open for. This allows for a high influx of sodium into the neuron which makes the neuron's internal membrane potential more positive. After reaching a certain threshold of around −55 mV, the neuron will fire an action potential. The voltage-gated sodium channels subunit 4 detects the voltage potential difference in extracellular space and opens the channel to allow the influx of ions. It is cited that at least a 1 mV/mm voltage gradient is needed to affect neuronal spiking. Since the electrodes on the device are placed on the outside of the head, noninvasively, the current will be attenuated by the skin and skull by roughly 75-95%. Therefore, in some embodiments, 4-6 mA should pass through the brain to induce a 1 mV/mm voltage gradient in a specific region of interest.

However, current levels higher than ~3 mA will cause skin reddening due to high charge densities if a single electrode is used. Embodiments seek to minimize this effect. Embodiments can take advantage of the capacitive properties of neuronal and/or glial cell membranes to implement a charge integrating mechanisms from an electrode, temporally integrated in such a manner that if implemented faster than the time integrity constant 1-100 mS, the neuronal and/or glial cell membrane will feel a summated voltage gradient. In embodiments, the charge integrating mechanisms are polarity dependent, which allows for negation of fields in the brain with the summed effect on neurons or glial cells being zero or close to zero. This property allows embodiments to create region-specific stimulation with areas surrounding the regions that have a charge distribution of zero or close to zero.

FIG. 1A is a perspective view of a wearable electrical stimulation device 10 (headset) having a wrap-around design. Embodiments can include wearable devices that wrap around the patient's head anteriorly, posteriorly, superiorly or any combination thereof. Stimulation device 10 has a body 12 that includes a housing and any electronics used to drive electrode arrays 14. In some embodiments, the stimulation device is a self-contained wireless headset that includes onboard power and controllers that can be pre-programmed or controlled in wireless communication with an external processor (such as a laptop/PC, server, mobile device, or cartcomputer). In some embodiments, the processor (whether external/remote or onboard, or the onboard controller runs a therapeutic routine guided by software instructions and by information within a medical records database system, which may be accessed wirelessly/over a network. In some embodiments, an external processor accesses patient records, creates a therapeutic plan, and loads that plan into memory of stimulation device 10 over a removable USB connection or wireless connection.

In some embodiments, the therapeutic plan is adapted to each patient based on medical history, symptoms being treated, and by individual patient anatomy. In some embodiments, medical imaging (CT/MRI/ultrasound) can be used to identify the specific location of the thalamus relative to the headset or to anatomical landmarks to which the headset can later be oriented. For example, once a stimulation headset is placed on a patient's head, an ultrasound device can be used to confirm placement of the stimulation electrodes relative to relevant brain anatomy. This can be used to calibrate the generation of electric field gradients from the electrode arrays to more accurately limit treatment areas to the most relevant. This targeting information can then be used to modify the specific treatment plan and send the updated targeting geometry to the onboard controller. In some embodiments, assumptions are made about patient cranial anatomy relative to headset placement and a preloaded field targeting routine can be used. In some embodiments, one of several pre-generated targeting profiles can be selected based on statistically relevant patient criteria, such as head circumference, age, gender, etc.

Once a headset is placed on a patient and the location of brain anatomy relative to electrode array location is assumed or determined, subsections of each electrode array can be energized to apply a current between the electrodes. By creating transcranial (e.g., bilateral) pairs of sections of electrodes, the location of the most intense part of the intervening field or current can be targeted to affect certain parts of patient tissue. By iteratively firing different subsection pairs, the additive field over time can be shaped. By firing different subsection pairs faster than the time integrity constant of the neuron, 1-100 ms, the electric field gradients sum such that the neurons feel a voltage potential equal to all of the electric field gradient passing over it while the area of the skin under the electrode feels a fraction of the current. This can allow for higher current levels to reach deep regions of the brain safely to depolarize neurons without harming the skin. Some of the main deep cortex regions/tracts in the brain that, if targeted, can help alleviate symptoms of a variety of disorders include: central thalamic nuclei, corticospinal tract and columns, substantia nigra, subthalamic nucleus, nucleus basalis of meynert, globus pallidus internal and external, and nucleus accumbens.

Figure 1B:
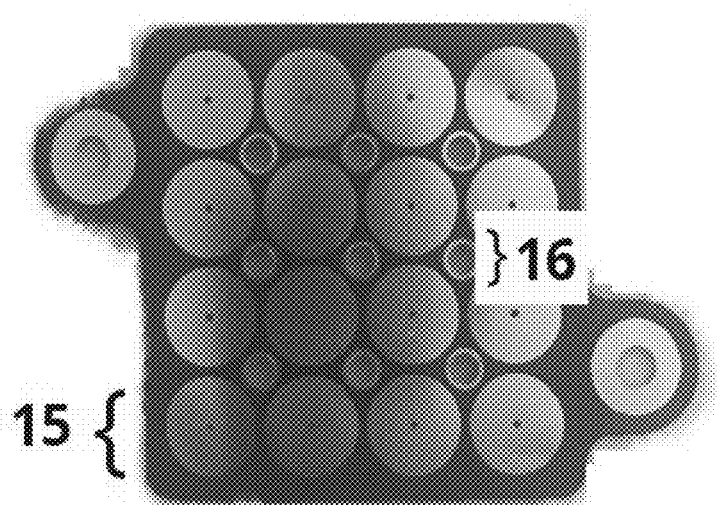
FIG. 1B is a side view of an exemplary electrode for use with some embodiments.

In some embodiments, each electrode array contains at least 64-128 gold, stainless steel, or copper pins called sub-electrodes. In some embodiments, the electrode array is 4-12 cm×1-4 cm while in other embodiments the electrode ranges from 1-by-1 in. to 5-by-5 in. in size. In some embodiments a range of 1.5-2 in sizes provides sufficient sizing to target ROI best. In some embodiments, the subsets of electrodes are groups of electrodes within each array in the circumferential direction of the patient's head (i.e., spaced anteriorly and posteriorly relative to other subsets) and the sub-electrodes range from 0.1-by-0.1 in. to 1-by-1 in size. In some embodiments, subsets may also be spaced, in part superiorly and inferiorly, allowing targeting of the patient's tissue in three dimensions. Sub-electrodes may have a 0.1 to 2 cm protrusion (0.5-10 may be preferred in some embodiments) to allow for sub-electrodes to make scalp contact as they rummage around hair follicles. In some embodiments a protrusion of up to In some embodiments, each electrode array will have sub-electrode of various sizes such as 15 (large sub-electrode) and 16 (smaller sub-electrode) in FIG. 1B. Electrodes and sub-electrodes can be made from a wide variety of conductive materials and flexible circuits to account for different head topology. The most suitable material to develop the electrodes are silver chloride, silver, gold, stainless steel, or another metal compound that can conduct electricity with low temperature sensitivity.

FIGS. 2A-2D illustrates an exemplary firing pattern for subsets of electrodes in each bilateral array, in one embodiment. One cycle of the exemplary firing pattern all happens within 1 millisecond, with the pulse length; the on/off time of the waveforms coming from each electrode subset can be varied with several values. All pulse lengths should be equal in length to properly cancel out. In this example, each electrode array is divided into four subsections for illustration. In different embodiments, larger amounts of subsections can be used. In some embodiments, they can be dynamically or statically sized such that each subsection has the same or differing numbers of electrodes. In some embodiments, electrodes can belong to more than one subset.

FIG. 2A shows the electrode firing pattern at time step T1 and T1+Δt. Opposing electrode subset pairs E1 and E3 are firing sequentially according to the following. Electrode subset pair E1 turns on to generate an electric field gradient with a current magnitude of 1.25 mA, with the left electrode subset acting as a cathode. Electrode subset pair E1 turns off. Electrode subset pair E3 turns on, to generate an electric field gradient with a current magnitude of 1.25 mA, with the left electrode subset acting as a cathode. Electrode subset pair E3 will then turn off. The Region of Interest (ROI) will have a multiplexed electric field gradient with current magnitude of substantially less (0.125-0.625 mA magnitude, in some embodiments) than the electrode input current due to skin, fat, and skull attenuation. In some embodiments, electrode signals provide sufficient voltage and current to introduce a voltage gradient of at least 0.8-1.2 mV/mm in the region of interest in the brain, as can be accomplished via any method accessible to a person of ordinary skill, such as cadaver measurement or simulation to determine the appropriate input signals for a given electrode design and reasonable range of patient anatomies. The region directly around the region of interest (ROI) will have a superimposed current magnitude of <0.125-0.625 mA, as felt by the brain tissue. The electric field gradient lines between pairs E1 and E3 each have a net current magnitude during the cycle of 1.25 mA between the electrode pairs.

Figure 2B:
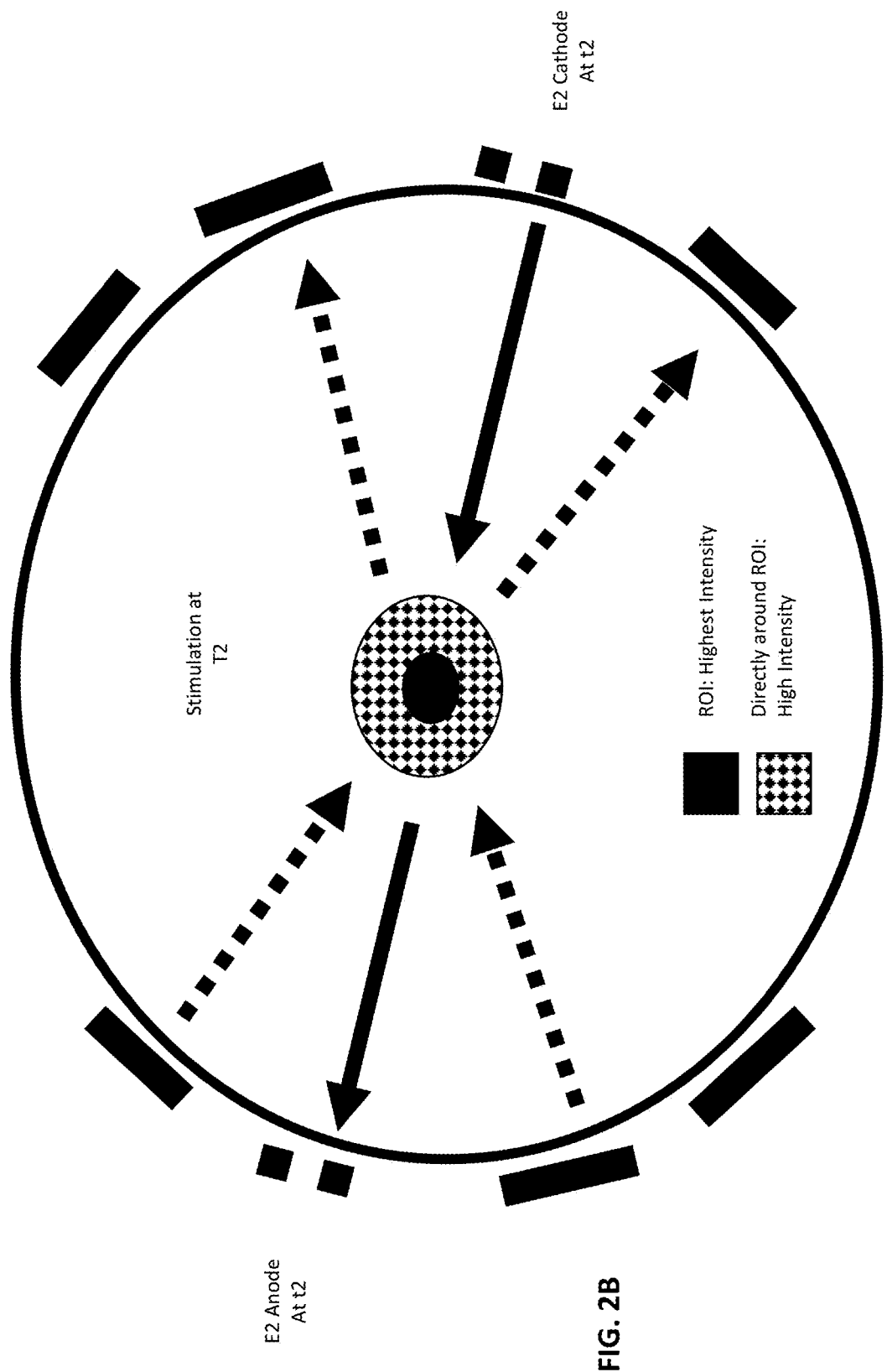

FIG. 2B shows the electrode firing pattern at time step T2. Opposing electrode subset pair E2 fires according to the following. Electrode subset pair E2 turns on with the opposite polarity compared to E1 and E3 at T1 and T1+Δt (cathode to the right) with the same current magnitude at 1.25 mA. The resulting electric field gradient polarity is indicative of whether the neurons in the ROI in the electric field gradient will hyper-polarize or hypo-polarize. By modifying the polarity of the net charge or current magnitude value with biphasic current, one can change the range of the polarization embodied by the neurons positively towards depolarization (hypopolarization) or negatively, further away from depolarization (hyper-polarization). If the electric field gradient generated by subset electrode pair E2 is opposite in polarity to the electric path generated by subset E1, the ROI now has a net current magnitude of 1.25 mA, and the current polarity from pair E2 is the opposite from E1 and E3 at T1 and T1+Δt and partially cancels that from E1 and E3. The region directly around the ROI now has an electric field gradient with current magnitude of <0.0625-0.3125 mA, as felt by brain tissue, a value determined by how much of the current is lost due to skin, fat, and skull attenuation. The field path between electrode subset pairs E1 and E3 has a net current magnitude, unchanged, of 1.25 mA.

Figure 2C:
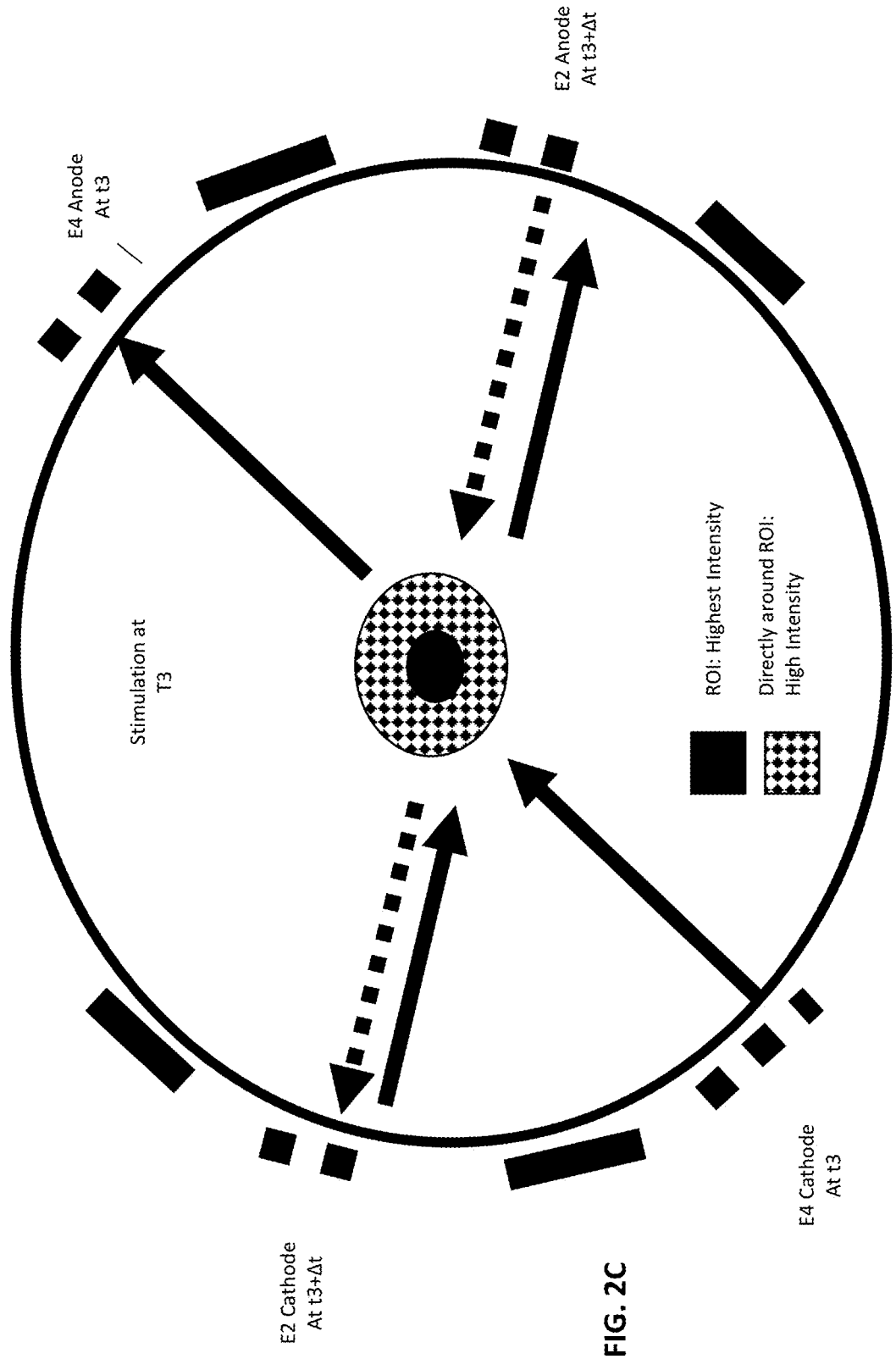

FIG. 2C shows the electrode firing pattern at time step T3. Opposing electrode subset pairs E2 and E4 fire according to the following. Electrode subset pair E4 turns on with the same polarity as E1 and E3 at T1 (cathode to the left) with a current magnitude of 1.25 mA. Electrode subset pair E4 turns off. Electrode subset pair E2 fires with opposite polarity (cathode to the left) than at T2 with current magnitude of 1.25 mA, causing a net charge of 0 along this path. The ROI will then have a net superimposed electric field gradient current magnitude of 0.1875-0.9375 mA, as felt by the brain tissue; or rather, 3.75 mA multiplied by 75-95%, a value determined by how much of the current is lost due to skin, fat, and skull attenuation. The region near the ROI will have a net current magnitude of <<0.1875-0.9375 mA; or rather, 3.75 mA multiplied by 75-95%, a value determined by how much of the current is lost due to skin, fat, and skull attenuation. The current magnitude in the electric field gradient path from the electrode subset pair E2 will be ~0 mA.

Figure 2D:
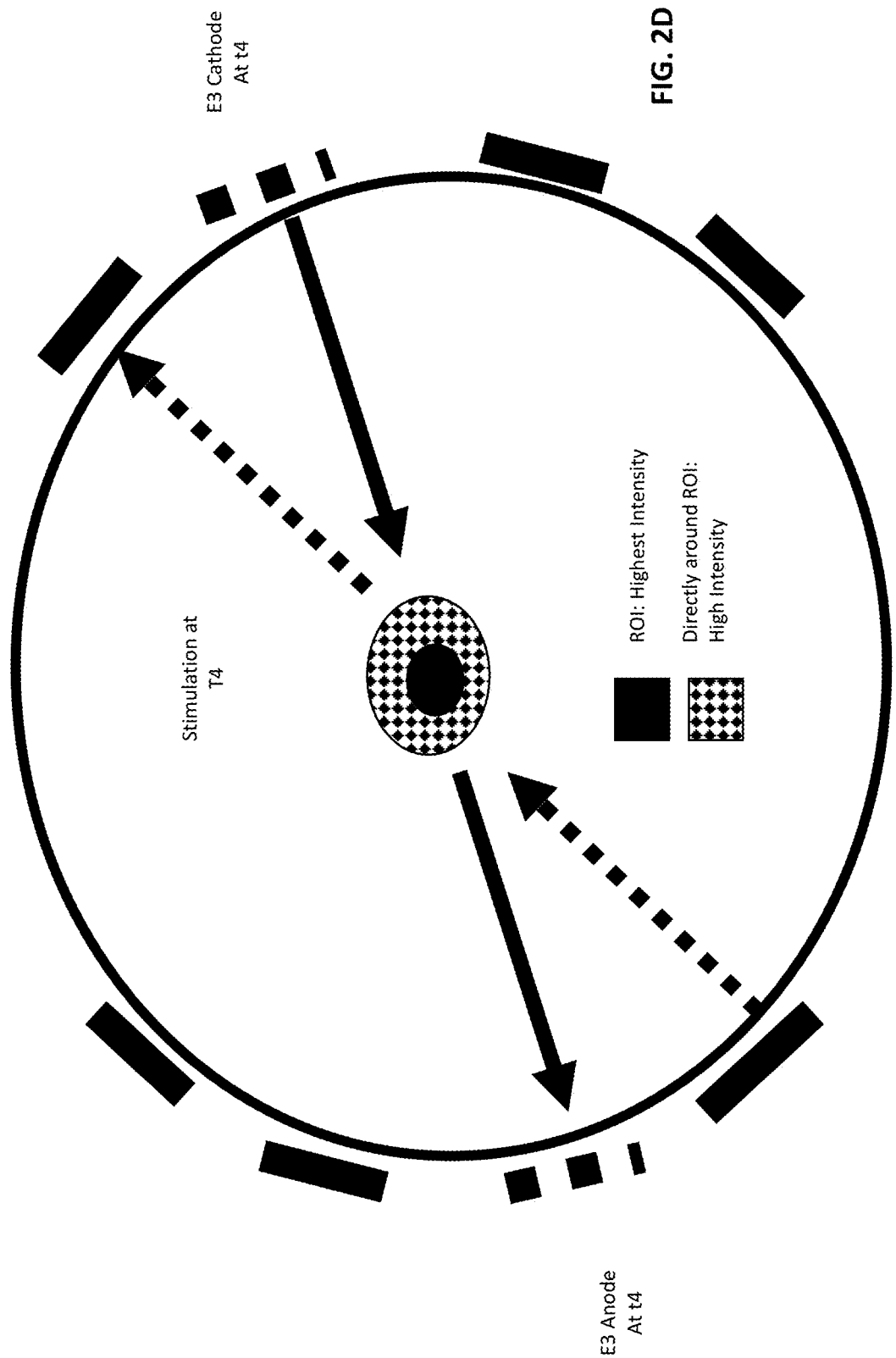

FIG. 2D shows the electrode firing pattern at time step T4. Opposing electrode subset pairs E3 and E4 fire according to the following. Electrode Pair E3 turns on to generate an electric field gradient with a current magnitude of 1.25 mA with the opposite polarity compared to E3 at T1 of FIG. 2A (cathode to the right), causing a net charge of 0 along this path. The ROI now has a superimposed current magnitude of 1.25-0.625 mA, as felt by the brain due to skin, fat, and skull attenuation. The region directly around the ROI has a current magnitude of <<1.25-0.625 mA, as felt by the brain due to skin, fat, and skull attenuation.

Over time the ROI and the region near the ROI will have differing current intensities, resulting in the ROI having higher current magnitude needed to depolarize neurons while the region near the ROI will have a lower current magnitude for subthreshold stimulation. In electrophysiology, the threshold potential is the critical level to which a membrane potential must be at so it can depolarize and induce an action potential. Neurons have a resting potential of −70 mV and will depolarize when the potential reaches −55 mV. Subthreshold stimulation refers to when the resting potential change induced by the electric field gradient does not exceed −55 mV, or rather, is less than −55 mV. When the potential is less than −55 mV, the neurons will not depolarize, and it will not induce an action potential. In some embodiments the stimulation method of FIGS. 2A-D will iterate through T1-T4 a total of four times in under 1 ms. 1 ms-100 ms is the time integrity constant of the neuron (i.e., the time needed for the neuron to return to resting potential). Exploiting this time integrity constant is shown to place a higher magnitude current into the brain to depolarize the neuron but not burn the skin or cause phosphines or headaches. The region near the ROI increases and decreases in current magnitude and size over time, elucidated with the growing/shrinking ovals at every time interval in FIGS. 2A-D.

Some embodiments utilize a different stimulation cycle, as shown in FIGS. 3A-3F with associated times steps T1-T4. These figures show an exemplary methodology for creating a roughly rhomboid section of patient tissue that receives a net injected current that exceeds the neuron stimulation threshold for therapeutic effect. The cycle in which time steps of the electrode and/or electrode subsets fire to generate electric field gradients of varying geometry as depicted in FIGS. 3A-3F with T1-T4 occurring in under 1-100 milliseconds, in some embodiments, with the pulse length of each time step are equal. T1-T4 all occur under 1-100 milliseconds because of the time integrity constant of the neuron which allows for the control of the polarization state of the neurons if the stimulus acted upon it occurs in the time frame of 1-100 millisecond (the time integrity constant). This method utilizes asymmetrically sized subsets of the electrode arrays on either side of the patient. A smaller subset of electrodes from each bilateral array can be paired with a larger subset of electrodes with the other bilateral array, causing a triangular spread to the current that stimulates patient tissue. Any irritation near the smaller side of the asymmetric pair of subsets due to increased current density can be mitigated by increasing the size of that subset. Embodiments using the method shown in FIGS. 3A-3F can utilize densely spaced electrodes to limit the amount of skin burning or irritation.

Embodiments can use a dynamic array where, for each individual electrode or subset of electrode, voltage, current magnitude, polarity, and frequency can be selectively controlled by software that runs the controller for the headset. Dense array allows for limited current bottlenecks to limit skin burning and tingling.

Figure 3A:
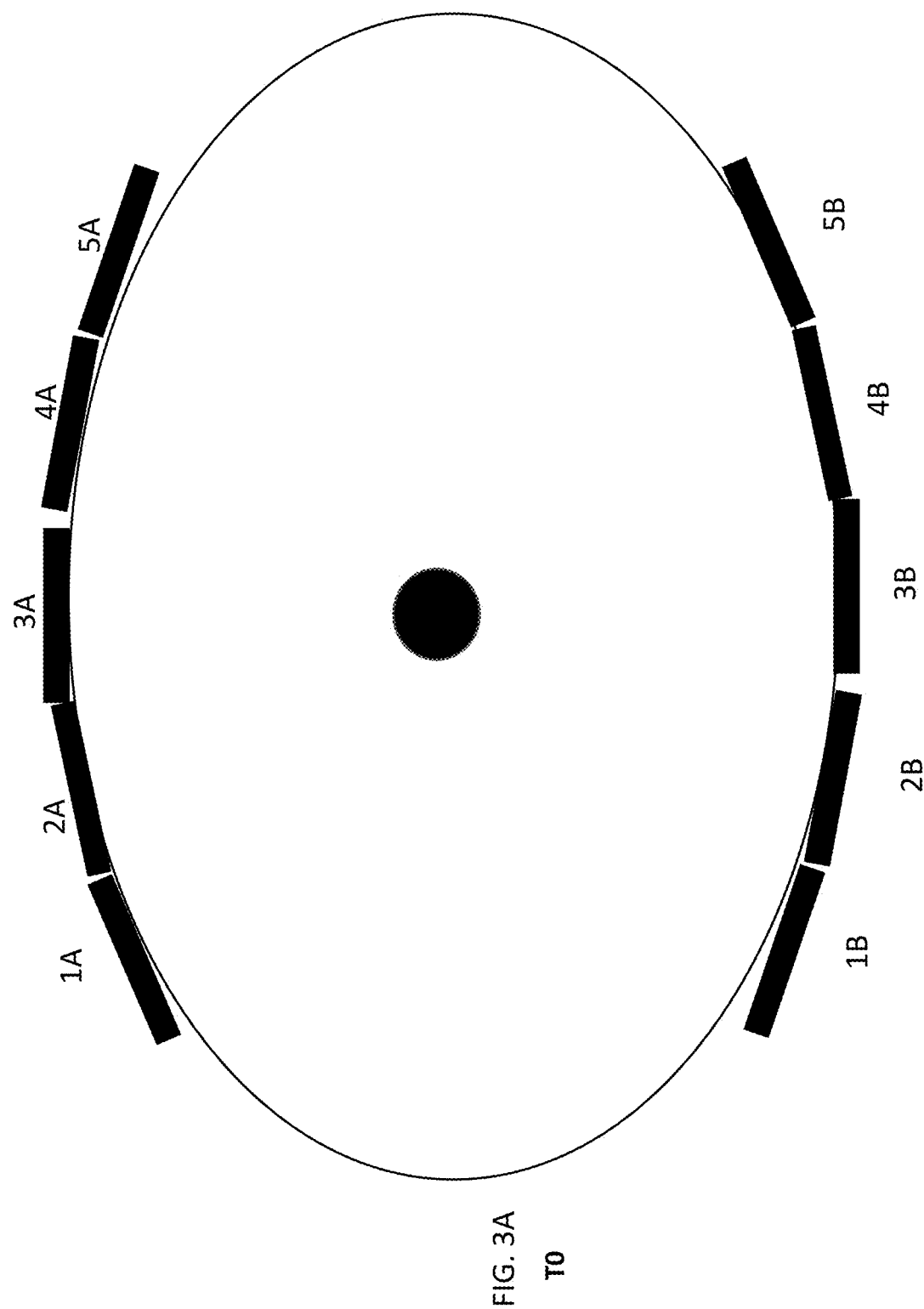
FIGS. 3A-3F is a representation of an exemplary firing pattern for subsets of electrodes in each bilateral array for use with some embodiments.
Figure 3B:
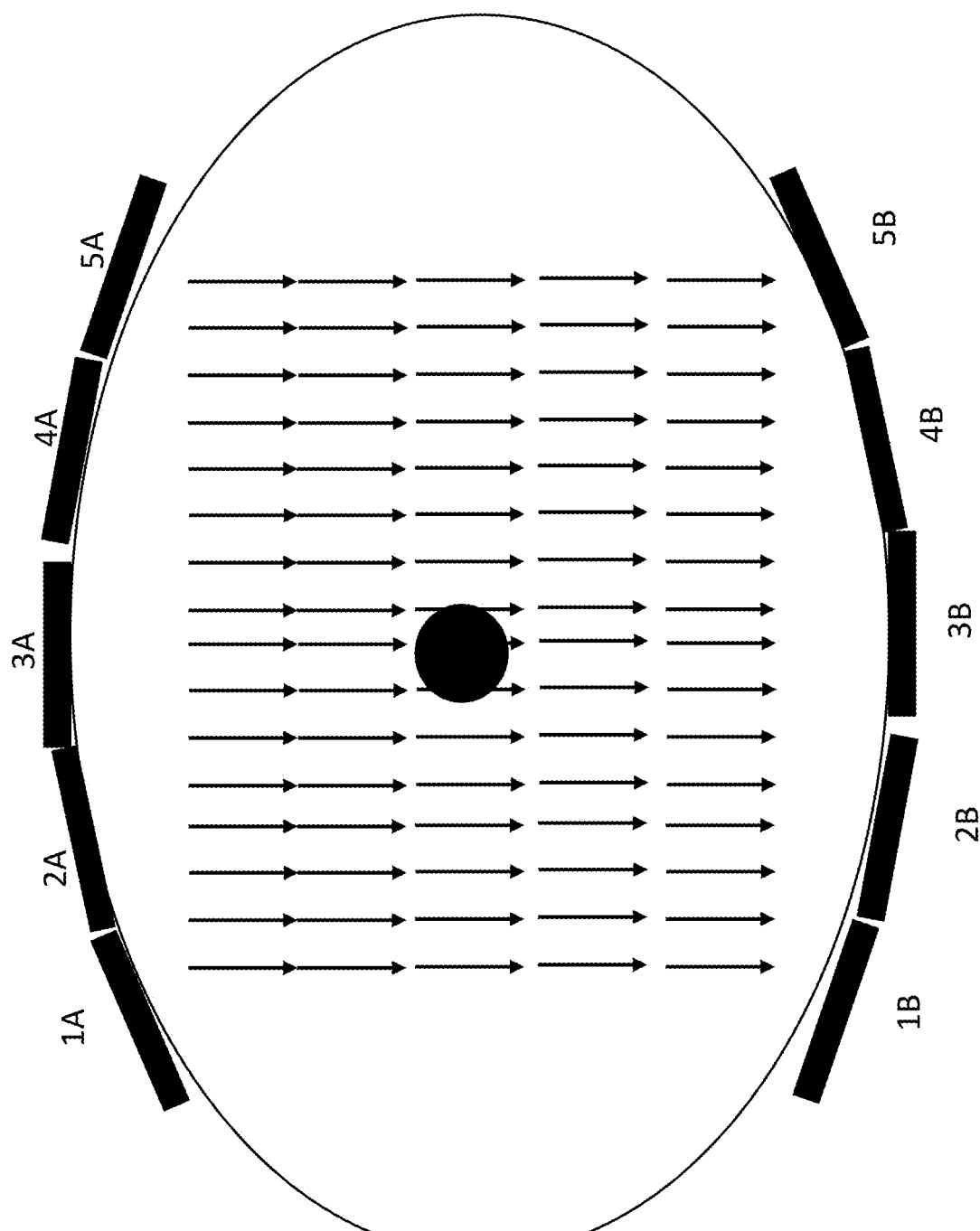

FIG. 3A shows exemplary electrode subsets within each bilateral array (oriented with electrode array A at the top and electrode array B at the bottom, in this example). For illustrative purposes, five subsets are shown for each array. In practice, more subsets of varying (statically or dynamically) sizes/numbers of electrodes can be used. FIG. 3B shows a first step at time T1. All electrodes fire from one side of the brain to the other, creating an electric field gradient with homogeneous properties from array A to array B (array A acting as a cathode, array B as an anode). This electric field gradient with current magnitude of 2 mA or less generated has a singular polarity across a certain area of the brain.

Figure 3C:
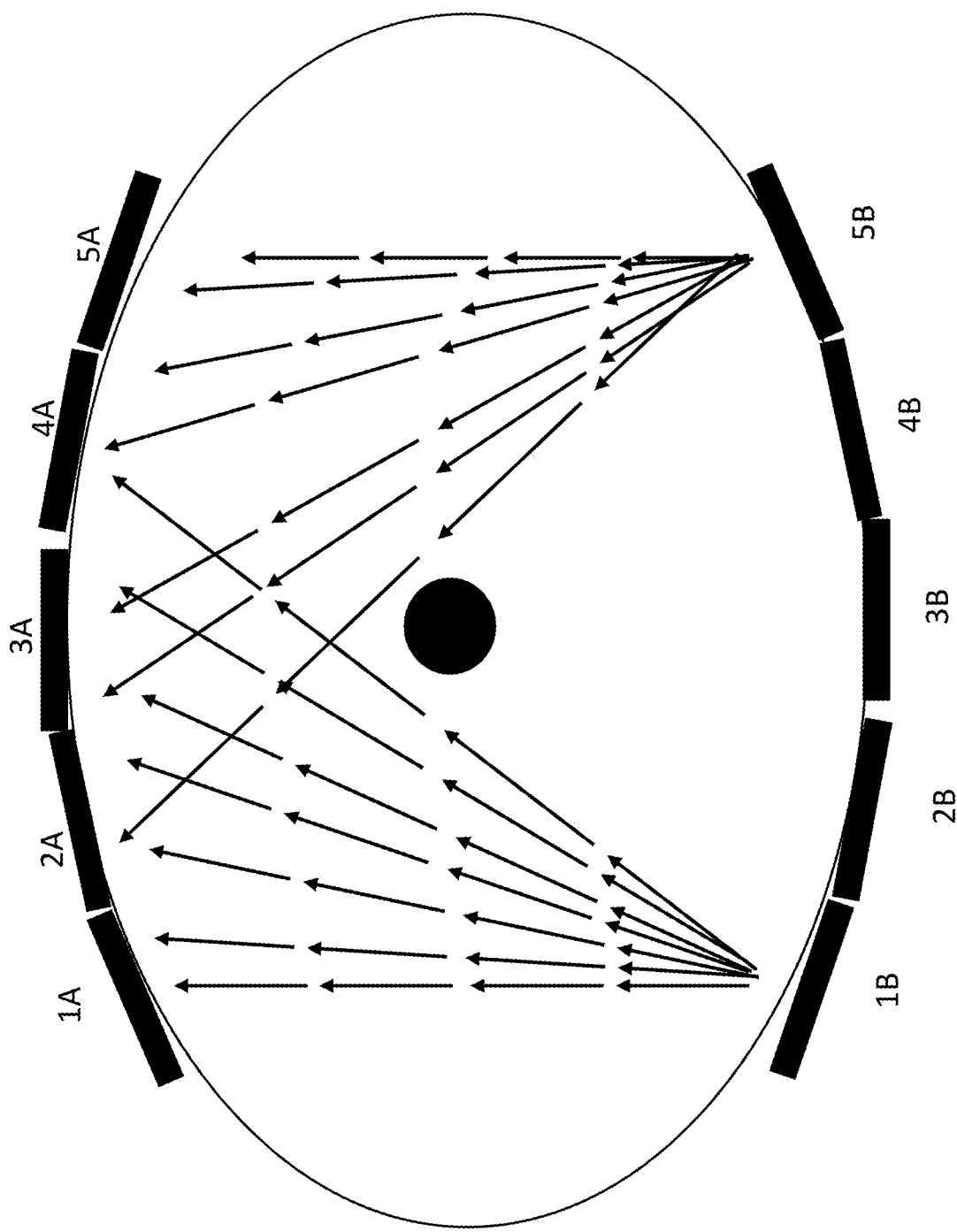
Figure 3D:
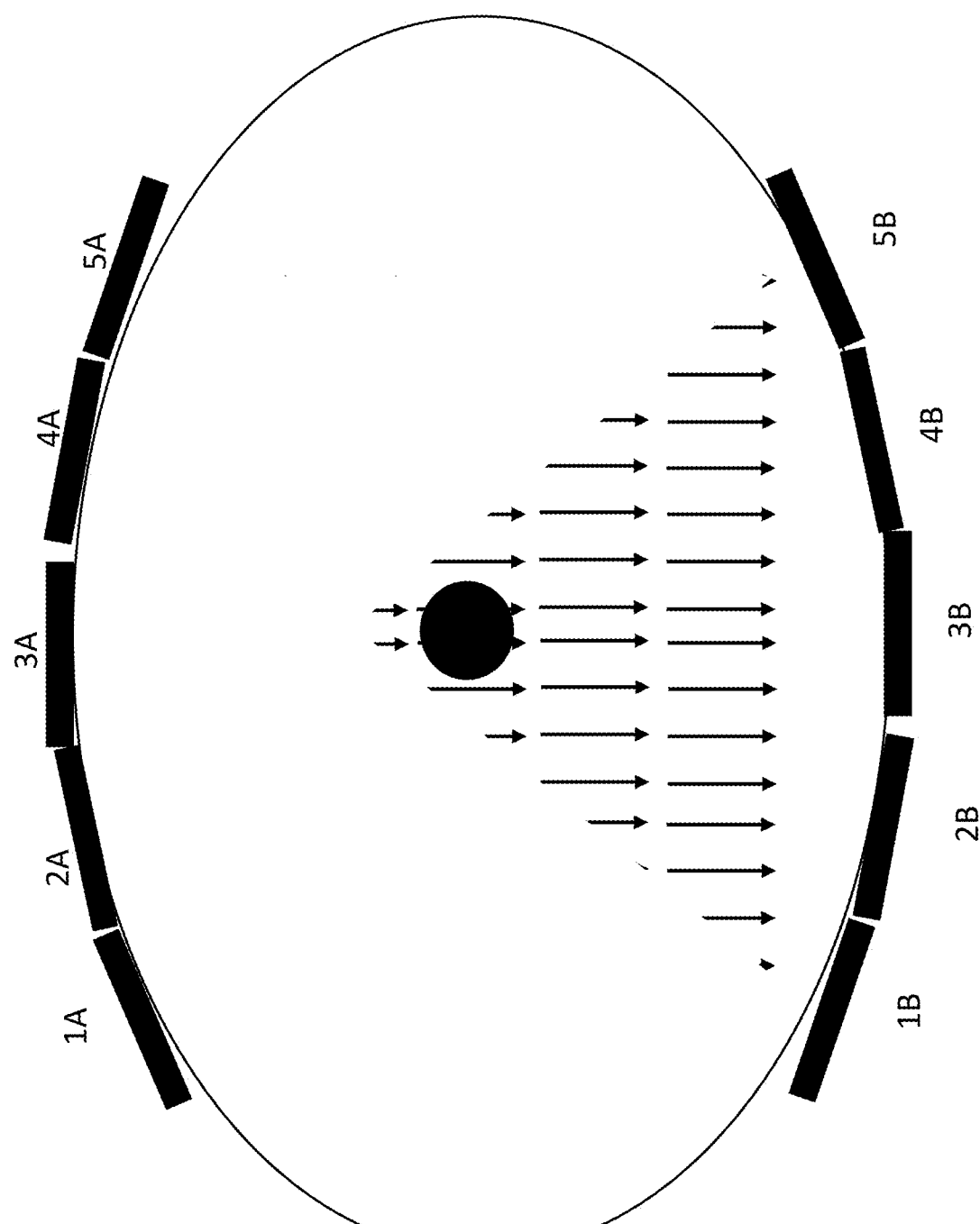

FIG. 3C shows two separate time steps at time T2 and at T2+Δt. At T2, electrode subsets 1A-4A (anodes) at T2, 1B (cathode) generate an electric field gradient to partially negate the large field generated at time T1. The electric field gradient generated here are not fields with homogenous properties. The shape of the field allows for some parts of the original field generated to be maintained while other parts are negated with a net charge of 0 or close to 0. The current density of the electric field gradient near 1B will be greater than the current density of any area of the electric field gradient generated at T1 of FIG. 3A. However, the current density changes are negligible and small; while the negation of charge from the previously generated electric field gradient by the electric field gradient generated at T2 is not completely uniform, it is close to being equal, which allows for the neurons under any region under the overlapping electric field gradients to have minor subthreshold potential change or 0 threshold potential change. This is done until a desired electric field gradient with associated current magnitude is maintained for the brain to respond to. In different embodiments, different field shapes can be generated. In this example the ultimate net field generated is a rhomboid-like field in the center of the brain, as will be shown. At T2, electrodes apply a non-uniform field of opposite polarity of the field at T1, of an area that is less than the original area covered by the first field at T1, but partially overlapping to negate the potential applied to neurons at T1. FIG. 3D shows the approximate net field that various portions of tissue are exposed to by the sum of T1 and T2. Electrode subsets 1A-4A (anodes) at T2, 1B (cathode) turn off. At T2+Δt, which occurs a little time after the sub-cycle occurring at T2 finishes, electrode subsets 2A-5A (anodes) and 5B (cathode), generate an electric field gradient with properties similar to the electric field gradient generated by the electrode subset 1A-4A (anodes) at T2, 1B (cathode). The geometry of the electric field gradient generated by electrode subset 2A-5A (anodes) and 5B (cathode), is a mirrored version of the electric field gradient generated by electrode subset 1A-4A (anodes) and 1B (cathode) at T2.

Figure 3E:
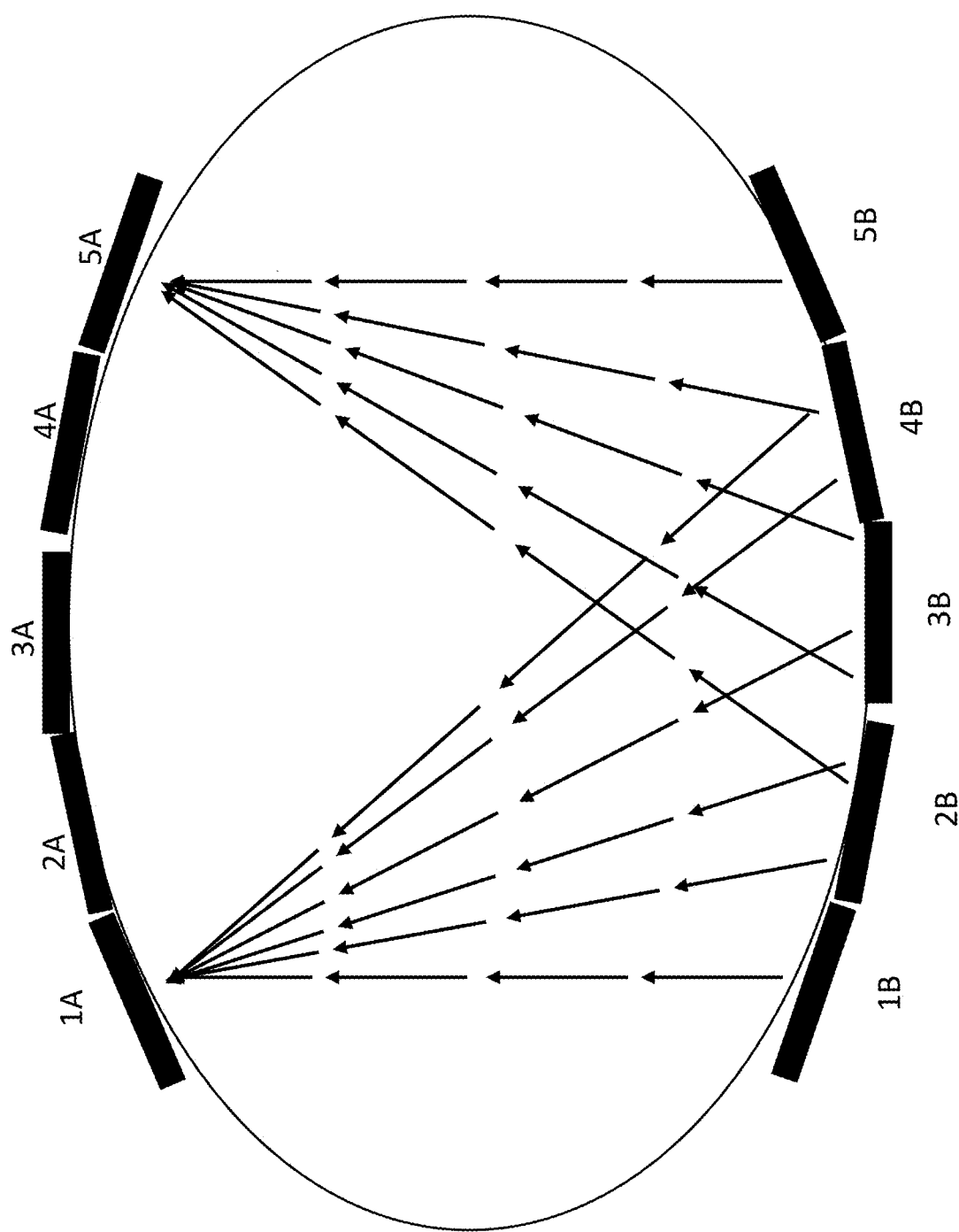
Figure 3F:
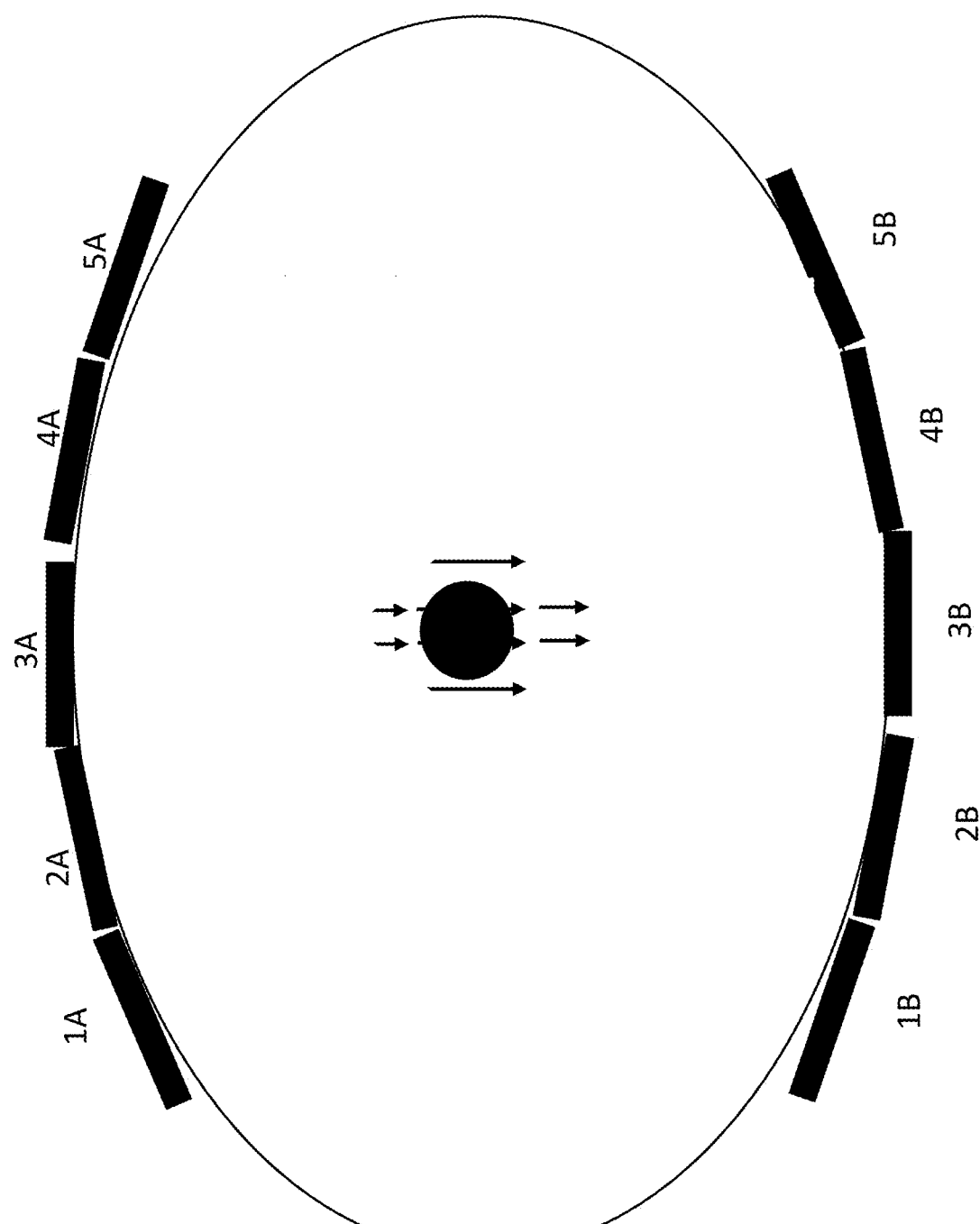

FIG. 3E shows a step at time T3 and T3+Δt. At T3, electrodes subset 1B-4B (cathodes), and 1A (anode) generate an electric field gradient to further partially negate the large field generated at time T1 like the field generated at T2 and T2+Δt. At T3+Δt, electrode subset 2B-5B (cathodes), and 5A (anode) turn on to generate an electric field gradient to further partially negate the large field generated at time T1 like the field generated at T2, T2+Δt, and T3. The geometry of the field generated at T3+Δt is a perfect mirrored version of the electric field gradient generated by electrode subset 1B-4B (cathodes), and 1A (anode) at T3. Step 3: like the field applied in FIG. 3C, the non-uniform field especially negates deep-tissue fields outside the target rhomboid. FIG. 3F shows the net final area at T4 that is not negated in the brain tissue as a sum of T1, T2, T2+Δt, T3, and T3+Δt. This is the area that is above the neuron stimulation threshold and is ideally located in the thalamus. These neurons will depolarize and induce action potentials. The example of FIGS. 3A-3E should all happen under 1 to 100 ms, which is the time integrity constant of the neuron.

The examples shown in FIGS. 3A-3F exploits the time integrity constant of the neuron (1-100 ms) which limits the amount of action potentials per second due to the absolute and relative refractory period. Limited amount of ions can flow in and out of the neuron and at a certain rate. The initiation of an action potential requires the neuron's internal membrane potential to reach a certain threshold (~55 mV) which requires a certain potential to be inside the neuron. The potential is modulated by the amount of positive ions within the cell relative to outside the neuron.

Embodiments that create a rhombus shaped pattern in the middle of the brain stimulate and counteract field potentials with four different triangles, as illustrated in FIGS. 3A-3F. Additional volumetric triangles of field potentials can be used to target in three dimensions, and some embodiments. The exact angles and dimensions of each triangular field created can be determined by the size of the respective electrode subsets being used to create each triangle. While the example shown in FIGS. 3A-3F used the entire array for the wide portion of the triangle, in some embodiments, a subset of the entire array could be used for the wide portion of the field triangle.

Figure 4B:
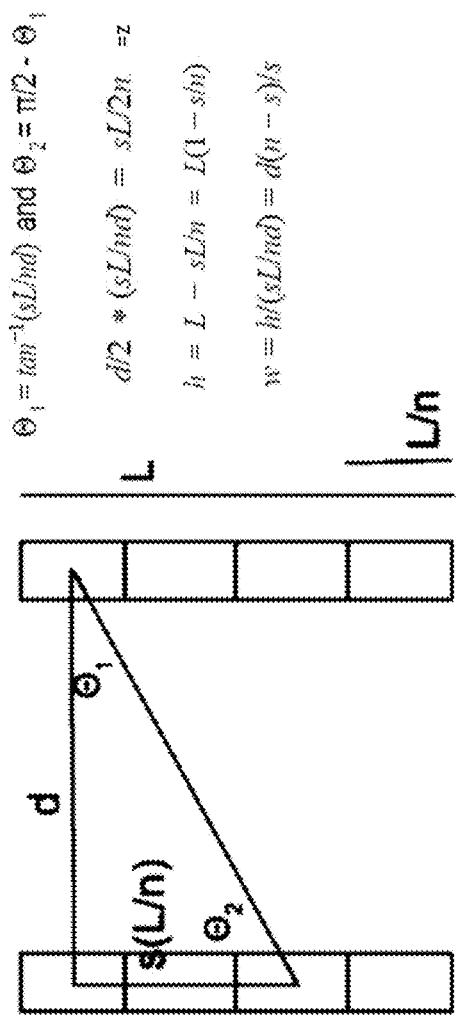
FIGS. 4A-4B is a geometric representation of an exemplary firing pattern for subsets of electrodes in each bilateral array for use with some embodiments.
Figure 4A:
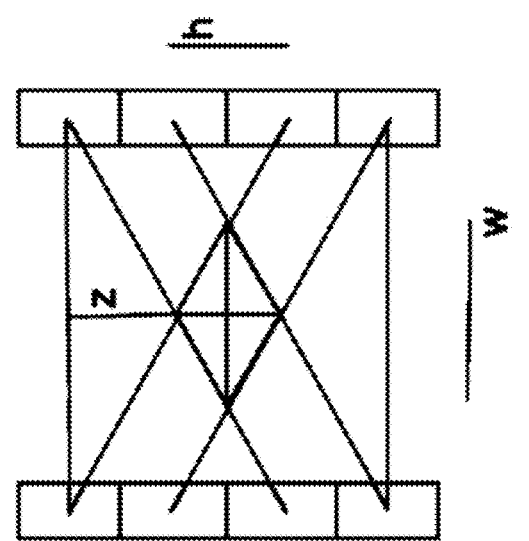

FIGS. 4A-B illustrates the geometry of the triangles to create the rhomboid of neurons that are stimulated above a stimulation threshold. It should be appreciated that the field exposed to tissue will be a gradient, rather than distinct triangles, but the fields above a certain threshold can be represented by triangles and a rhomboid.

FIG. 5 is a system diagram of a neural stimulation headset 100, which could include headset/electrical stimulation device 10. Headset 100 comprises a pair of bilaterally spaced electrode arrays 114 and drive circuit 116. Drive circuit 116 includes a processor 120 that includes memory and software to instruct controller 130 to try individual subsections of arrays 114. Note that the term controller can include the entire drive circuit including processor, memory, power source, amplifiers, etc. and any other circuit components needed to control the components in the headset. In some embodiments, headset 100 is a wireless device having its own on board power source 132 that provides power to the processor and controller. In some embodiments, processor 120 communicates with an external processor to receive instructions via communications interface 134. This can be a temporary removable USB port or a wireless networking device. Communications interface 134 can interact, in some embodiments, with a medical records system to download patient specific instructions to processor 120 during or before a procedure.

While embodiments have been described herein as transdermal, allowing the headset to be placed on the patient's skin, it should be appreciated that embodiments can also include devices where the electrodes are placed subcutaneously, or sub-cranially. The pulses described herein can range from 100 to 100,000 pulses per second and have current magnitudes that range from 0.01 to 8 mA per pulse. As further explained from henceforth, different pulse waveform parameters can be modified to modify the electric field gradients produced in the brain. Furthermore, electrodes can be scattered around a patient's head to target a specific region of interest or to generalize a field across a large region like the dorsolateral prefrontal cortex. So, the electric field gradients that can be delivered For example, one or more pairs of arrays of electrodes are arranged on a headpiece or band, galvanically isolated and driven by a driver circuit under microcontroller control. The array pair(s) are arranged to be placed on the head of a patient, spaced laterally, on opposite sides of the frontal lobe, namely on the left and right dorsolateral prefrontal cortex. The electrodes are configured to use transcutaneous electrical pulses with a required time-varying polarity change between a pair of bilateral electrode groups to stimulate structures in the frontal cortex to cause increases in interhemispheric coherence. This is done by increasing functional connectivity between cortical and subcortical networks as observed by an increase in myelination of axonal branches within these networks built by the anatomical landmarks described above. In some embodiments, a scattered electrode frame that optimizes current flow through the device reduces skin sensation and distributes current across several smaller, densely spaced electrodes. This allows for a compact distribution of electrodes on the head to reduce irritation and distribute current. Stimulation of the frontal cortex leads to increased connectivity to striatal regions through the fronto-striatal circuit. This, in turn, leads to an elevated decision-making process as the frontal cortex can hold more information at a point in time and send a more informed decision to subcortical regions to initiate an action the increased white matter integrity of frontal and subcortical regions.

As explained above, to induce spike activity, a voltage gradient of 1-1.5 mV/mm, coming from 4-6 mA, is generally needed. To do this, sending a sequence of discrete pulse packets such that the magnitude of all the pulses exceeds 4-6 mA when sent faster than the time integrity constant of the neuron, being 1-100 millisecond. For example, with arbitrary and modifiable, one can send 100 pulses with a pulse width of 0.05 millisecond and inter-pulse width of 0.05 millisecond and with a pulse amplitude (amplitude measure the current level in amperage) of 4-6 milliamps with each pulse to multiplex, or summate an electric field gradient of 4-6 mA (not considering skin and skull attention) in the brain, thus inducing an approximated 1 mV/mm gradient. In FIG. 1, the pulse width 1, pulse amplitude 2, inter-pulse width 3. The pulse width 1 provides us information about the amount of time the current is being sent through the electrode at a given pulse. As such, it is used to show how long the skin is being heated up per pulse and is used as a measure to ensure that no hazardous amount of current is being sent in to cause skin burning per pulse. The pulse amplitude 2 provides us information about the amount of current that is being summated per pulse in the brain as well as the amount of current that comes in contact with the skin per unit time. The pulse amplitude is an important value for directly measuring and creating a voltage gradient necessary to affect spike activity in the brain. The inter-pulse width 3 provides us information on how quickly the pulse amplitude 2 value is being summated in the brain and how many times per second the device is sending pulses. This is important to determine how quickly embodiments should send in pulses at a predetermined pulse amplitude to create a voltage gradient of a minimum of 1 mV/mm to induce spike activity. Pulse width 1, pulse amplitude 3, and inter-pulse width 3 can take on various values as long as the current levels on the skin do not go past ~8 mA and the total summated amplitudes of the all the pulse packets is greater than 4-6 mA when measured in 1-100 millisecond intervals.

Now transitioning from the last paragraph, the pulsed current described herein can range from 0 to 100,000 pulses per second, or stated as 0-100,000 Hz (with at least 10 Hz preferred), and with pulses having a width ranging from 0 to 1 second (depending on frequency and duty cycle), to allow enough time to multiplex current faster than the time integrity constant of the neuron which is 1-100 milliseconds to create voltage gradients of 1 mV/mm or higher in the brain. This allows for a safe depolarization of the neurons in the frontal cortex and ensures skin safety. The pulsed current described herein can have current magnitudes that range from 0 to 8 mA per pulse to ensure skin safety and have voltage magnitudes between 0-10 Volts to also ensure skin safety. To continue, the most optimal way to entrain brain rhythms to induce hemispheric coherence or maximize the associative connectivity between regions is through alternating current. As explained earlier, based on a study, a 10 Hz tACS frequency is used to best entrain alpha rhythms in the frontal lobe. This is due to the slow conduction velocity of a neuron that is inversely proportional to the length of the total signal propagation of a single, or collection of action potentials, running on back and forth across the frontal cortex in a given second. Interhemispheric coherence can be interpreted by analyzing the mutual relationship between two EEG signals across different frequency bands.

Figure 6:
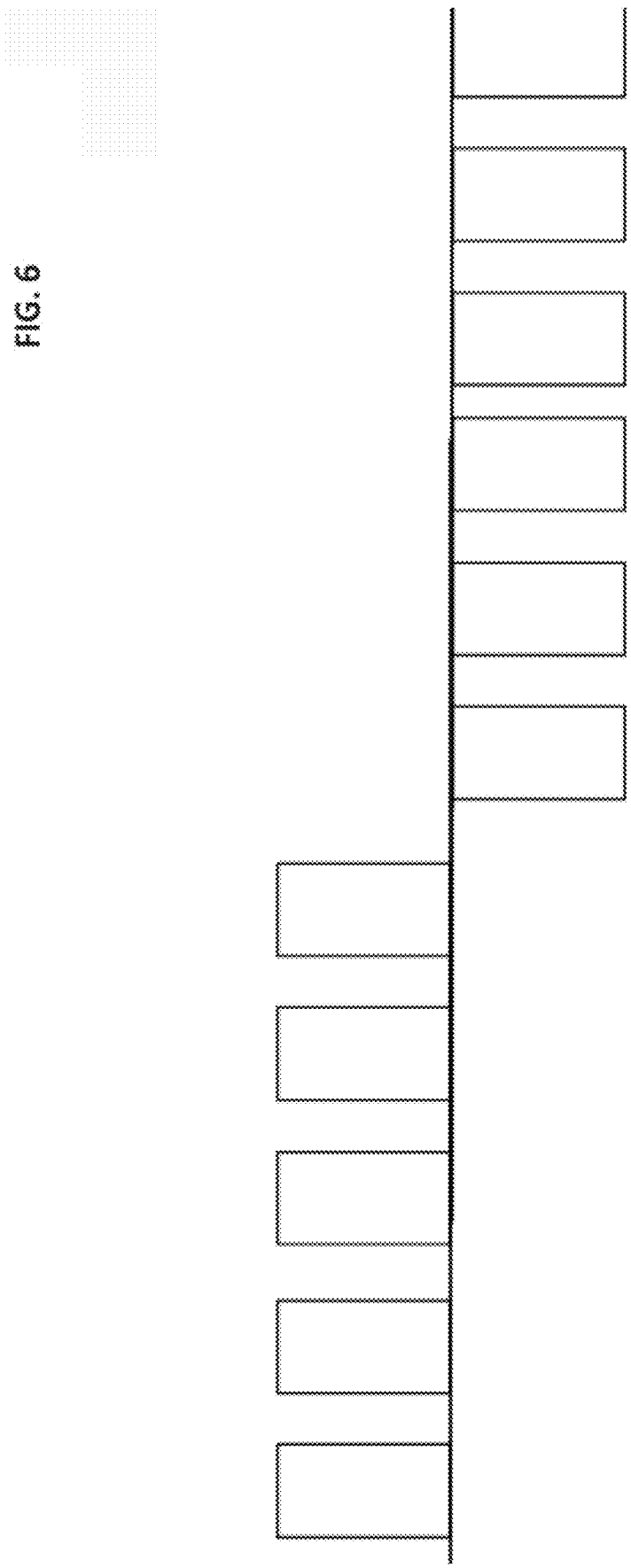
FIGS. 6, 7, 8, 8A, 9, and 9A are electrical graphs of exemplary stimulation pulse profiles for use with some embodiments.
Figure 7:
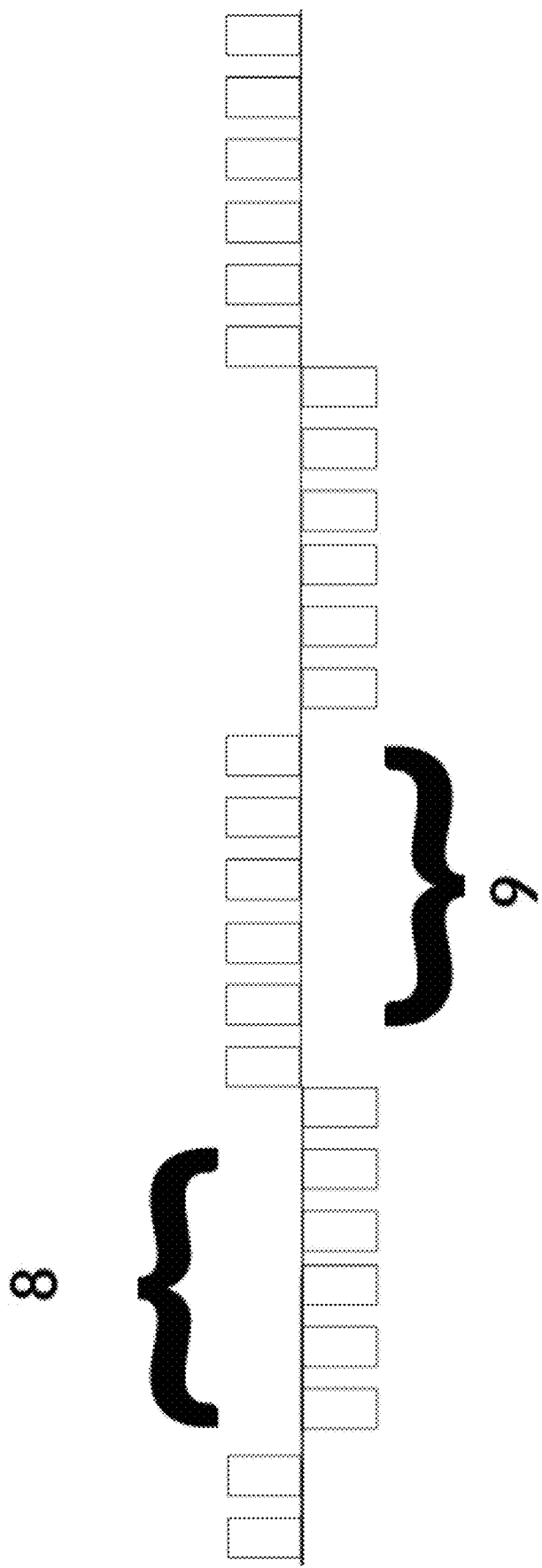

Another exemplary stimulation protocol can be characterized as Transcranial Alternating Pulsed Current Stimulation (tAPCS). one can create stimulation that utilizes the best of tACS and tPCS to optimize depolarization, best induced by tPCS, and optimize interhemispheric coherence, best induced by tACS. There are two methods to go about this which both will be cited in this patent. First, one can create a pulse sequence whereas the pulse polarity switches every 100 milliseconds such as FIG. 6 between a positive to negative voltage and vice versa. An extended image of the pulse sequence is seen in FIG. 7. What these resemble is a quasi-alternating current that travels with the natural alpha oscillations emerging from action potential propagation in the frontal cortex. This is not a perfect Alternating wave, as in FIG. 7, however, the polarity switching nature of the pulse sequence better induces interhemispheric coherence than any other transcranial stimulation system. To further expand upon this, if one wants to entrain a certain frequency in the frontal cortex, for example, 13 Hz, one would flip the polarity of the pulse sequence every 1000/13 millisecond, ~77 milliseconds, as shown by the brackets in FIG. 7 with bracketed items 8 and 9. It is important to induce interhemispheric coherence through a specific entrainment frequency to better help hemisphere connections to alleviate symptoms of affective disorders. So, the desired entrainment frequency can be used to calculate the time duration of the pulse sequence being emitted by the device before switching or reversing polarity. Thus, embodiments can entrain any frequency by deciding how quickly the pulse sequence send switches over time. This in turn leads to great fractional anisotropy values along anterior thalamic bundles and the forceps minor as 1) hemispheric communication increases due to polarity switching of the pulses and 2) fronto-striatal connections strengthen leading to more myelinated tracts for informed decision making.

Figure 8:
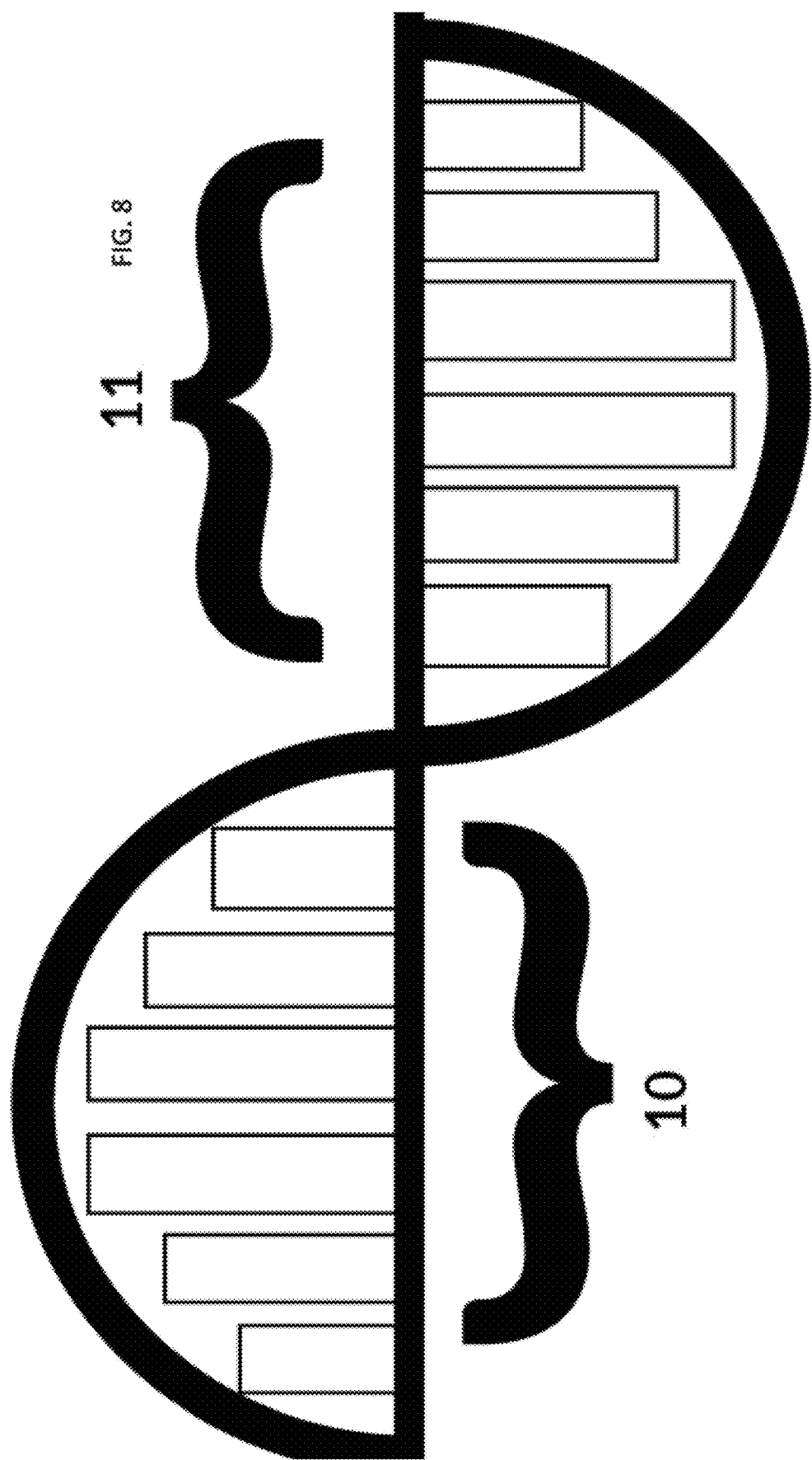
Figure 8A:
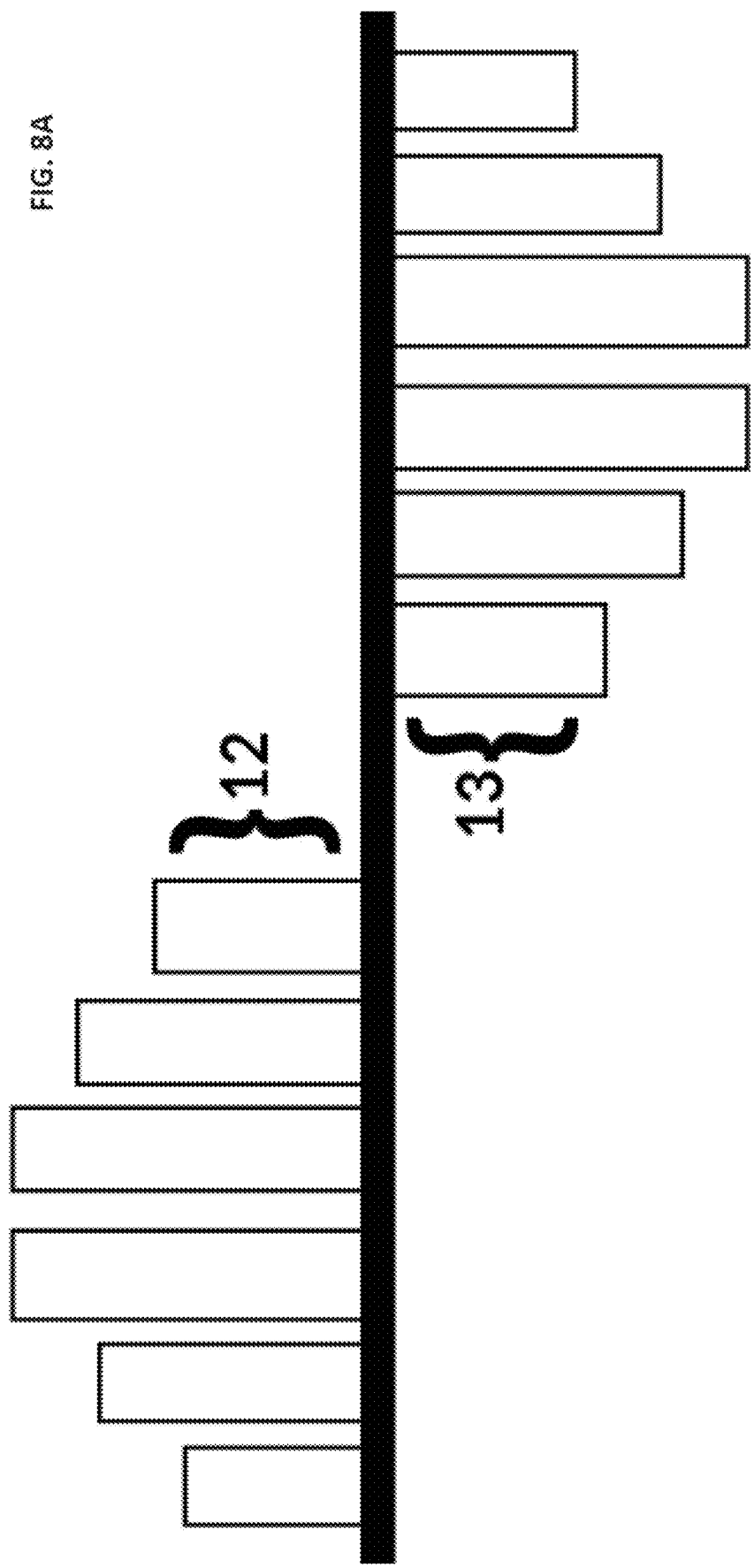
Figure 9:
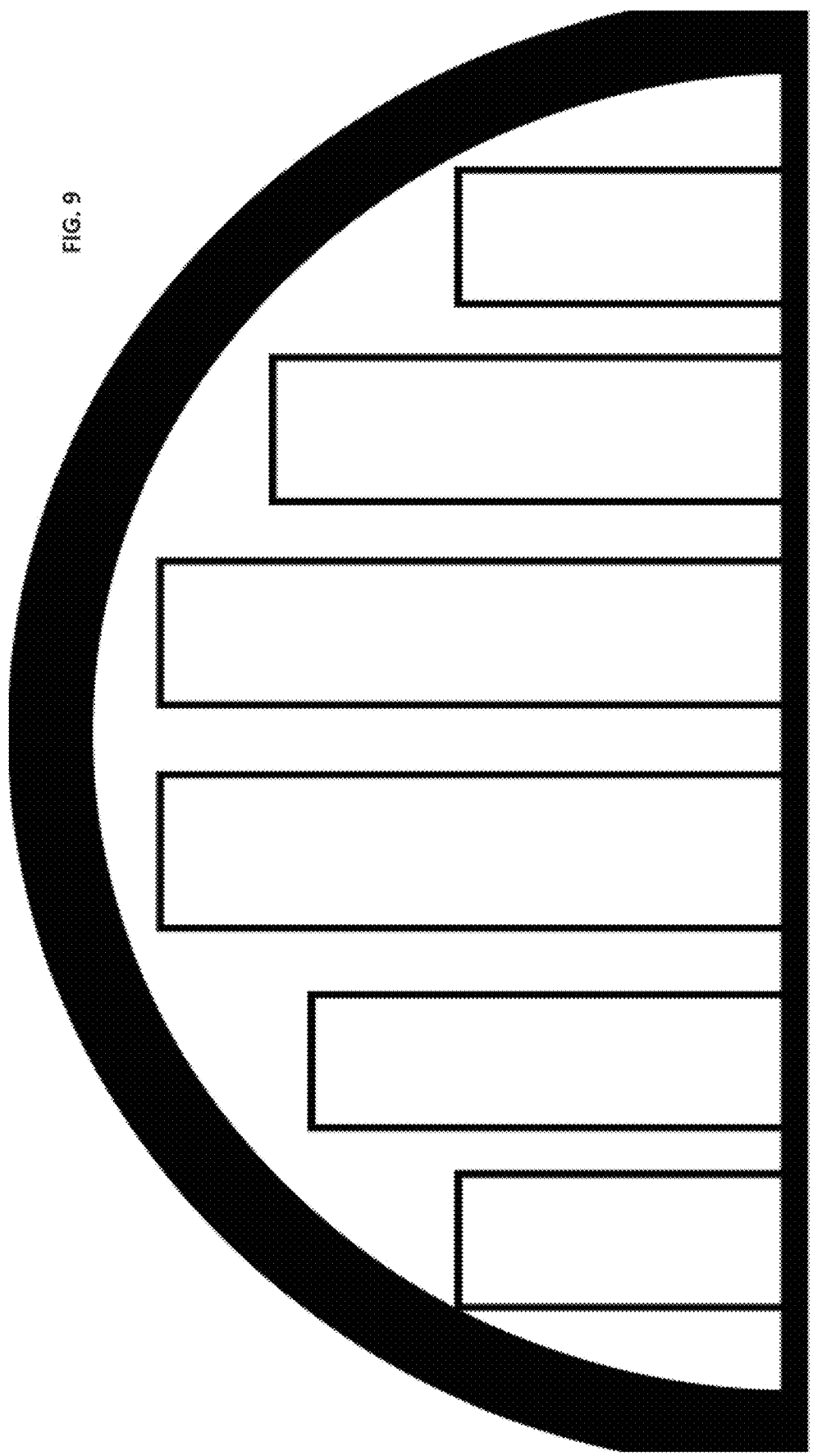
Figure 9A:
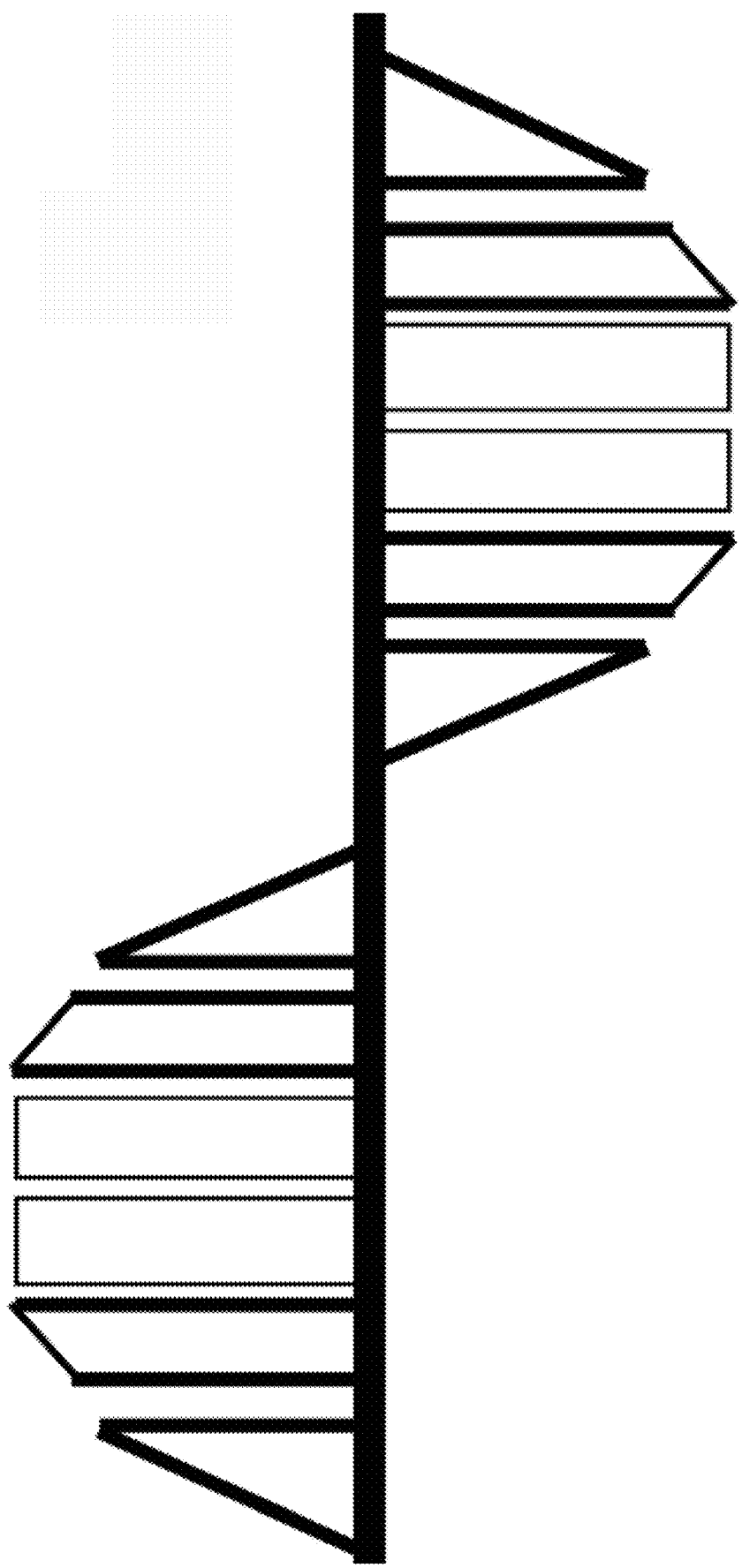

As one can infer, a square or rectangular pulse does not line up with a sinusoidal pulse. However, one can send a modified square wave, as shown in FIG. 8 to help create a pulse sequence in which the neurons in the brain interrupt as a quasi-sine wave, to further maximize the entrainment between the generated signals of the device and the natural oscillations of the brain. The period 10 and 11 in FIG. 8 represent the ongoing polarity change of the pulse sequence at a frequency correlated with the frequency embodiments are trying to entrain in the frontal cortex. FIG. 8A shows the ongoing pulse amplitude 12 and 13 change to model a sinusoidal pulse with discrete pulses. FIG. 9 shows the pulse sequence with one half of the period of the waveform. Pulses take on different amplitudes 12 and 13 overtime, whilst making sure the total current sent is under 6 mA, and that the modified waveform creates a discrete sine wave with a frequency equal to the frequency that we want to entrain in the frontal cortex. Furthermore, in FIG. 9, embodiments can further maximize the association between the discrete pulse sequence used to current summation/multiplexing in the brain to elicit depolarization by sending pulses in geometry that better fits a sinusoidal pulse. The geometries of the pulses shown in FIG. 9A are triangular 14, trapezoidal 15, and rectangular 16, however, other geometries and pulse shapes may be derived in accordance with the principles of the invention to accomplish the same objectives such as FIG. 9A. FIG. 9A is an extension of FIG. 9 showing the pulse sequence with both polarities. FIG. 9 conveys a deeper configuration of pulses that utilizes a more fractal geometry 17 of sequenced pulses to induce a sufficient current level to depolarize the neuron in the time scale of the time integrity constant of the neuron, being 1-100 mS, or 10-1000 Hz, whilst also obeying an overarching sinusoidal pulse shape with a frequency correlated to the entrainment frequency desired. Thus, instead of geometric pulses, embodiments can use a small half-period sinusoidal pulse 17 contained with a larger frequency. FIG. 9A is an extension of FIG. 9, this time showing both polarities of the pulse. In summary, one maximizes the entrainment to induce hemispheric coherence and depolarization of neurons by creating a hybrid alternating/pulse waveform as shown in the figures attached. This is done with ensuring that there is the highest safety to the user of the device.

In the embodiments herein, the electrodes and sub-electrodes can be dual functional in which the sub-electrodes can send different shaped waveforms into the brain for direct neuronal modulation and the sub-electrodes can record neuronal potentials via electroencephalogram (EEG) analysis. At least one amplifier is connected to the electrodes to intensify the EEG signals from the electrode and sub-electrodes. Since the network of electrodes and sub-electrodes can be arranged around the patient's head, EEG signals can be used to assess specific functional network abnormalities from distributed regions of the brain. A processor connected to the distributed electrode array generates the EEG signals which is then sent to a remote display. The display can be online in front of the user, at a hospital, and/or sent back to a remote server. A physician, specialized research technician, and/or data analysis engineer can use the EEG signals to assess, specifically, the connectivity in the user's brain to create customized waveforms to be used for stimulation. This will further personalize the product for the user's specific brain structural and functional connectivity by creating specifically shaped waveforms in accordance to the user's EEG signals. Furthermore, machine learning and artificial intelligence can optimize the closed loop EEG-TCS performance as well as assessing images of neural pathways using EEG Inverse reconstruction algorithms. Furthermore, Noninvasive Deep Brain Stimulation pulses can be created via EEG signal potentials to help alleviate symptoms in a variety of neuropsychiatric disorders.

In the methods described above, it should be noted that different pulses are used for different diseases at different times of the stimulation treatment protocol. Specifically, in Parkinson's disease, substantial physiological abnormalities can be measured in subcortical areas of the brain. Specifically, the substantia nigra and subthalamic nucleus are the two primary regions of interest that show the greatest pathology in Parkinson's disease, specifically, which leads to symptoms of the motor and non-motor types. The intervention of sending downstream spike trains via stimulating surrounding tracts can be accomplished with the pulse protocols that are outlined above and will continue to outline below. Specifically, the treatment of placing two electrodes, transcranially, on the motor cortex and two electrodes on the frontal cortex. Electrode placements based on the EEG 10-20 are F3+F4 on the frontal cortex and C2+C3 (if the Parkinson's disease's symptomatology is upper extremity dominant) or C4+C5 (if the Parkinson's disease's symptomatology is lower extremity dominant). The stimulation treatment protocol of this tAPCS paradigm is run for a minimum of 12 weeks. The electrodes can be fitted into a helmet or frame so that there is accurate placement of the electrodes onto the EEG regions. The first 3 weeks of the stimulation protocol, a 350-650 ms pulse with 30-70 ms interpulse break running at current levels of 2-4 mA will be sent back and forth between electrodes F3 and F4 for the first 5 minutes of the stimulation treatment protocol intervention. Every fourth 350-650 ms pulse will induce a polarity change in the code running the device to switch the cathode/anode electrodes between F3 and F4. This is helpful because 1) we want to induce tonic depolarization of neurons through a low values voltage gradient along the forceps minor in the frontal lobe through a long wavelength (350-650 ms) pulse stimulation and 2) we want to increase the fractional anisotropy of the forceps minor through a polarity switch in the current running between F3 and F4 every 4 pulses. In the next 15 minutes of the stimulation treatment protocol, a 30-70 ms length pulse with a 30-70 ms interpulse break running at a current magnitude ranging from 2-4 mA between electrodes F4 and C3 or C5 for 10 seconds will be induced through the circuit. Every 1-15 seconds, the current will switch from running between F4 and C3 or C5 to F4 and C2 or C4 with the exact same parameters in the pulse parameters. The anode, negative, electrodes will be F3 and F4 in the frontal cortex and the hind motor cortex electrodes will be the cathode, positive, electrodes. This second segment of the stimulation treatment protocol will be run for 15 minutes. The anode and cathode electrodes will switch responsibilities/polarity every 30-60 seconds in the 15 minutes of stimulation. The stimulation is when an electric field voltage gradient is created through pulsed stimulation across the corticospinal tract connecting the motor cortex to the frontal lobe, actions potentials will be induced in the neurons running along the tract and will be initialed all the way down the corticospinal tract and be sent to the subthalamic nucleus and substantia nigra. In the first 3 weeks, the total time for the stimulation treatment protocol is 20 minutes where the first 5 minutes of stimulation is the frontal lobe and the next 15 minutes of stimulation is between the frontal lobe and motor cortex.

In weeks 4-6 of the stimulation treatment protocol using tAPCS for Parkinson's disease, the 4 electrodes positions on the scalp/skull/brain may or may not be modified depending upon it the Parkinson's disease patient's symptoms shift from upper extremity dominant to lower extremity dominant or vice versa, thus, changing the hind motor cortex electrode positions between C2 or C3 to C4 or C5 respectively. A qualified research technician and/or qualified healthcare worker adjusts parameters after measuring clinical outcomes obtained from weeks 1-3 of stimulation treatment protocol through neuroimaging, psychometric/neurological assessments, and/or through neurological examination specific to Parkinson's disease. In weeks 4-6 of treatment, the pulse length in the first 5 minutes of treatment should reduce by 5-15% depending on the initial pulse length value chosen in weeks 1-3 to induce a higher voltage gradient value inside the brain in comparison to weeks 1-3. This will lead the brain to reach a plateau point of stimulation habituation and thus constantly allow the brain to adapt to different stimuli to increase the efficacy of the treatment for Parkinson's disease. The current magnitude in weeks 4-6 of the stimulation treatment protocol may increase or stand constant depending on the clinical outcomes obtained from weeks 1-3 of treatment with current levels increasing if no changes in the Parkinson's disease patient symptomatology occurred in weeks 1-3. An increase of current magnitude between the range of 2-4 mA may occur if no substantially positive change of symptoms occurred in weeks 1-3. The total time of the stimulation treatment protocol in weeks 4-6 still remains constant at 20 minutes where the first 5 minutes of stimulation is the frontal lobe and the next 15 minutes of stimulation is between the frontal lobe and motor cortex.

Figure 10:
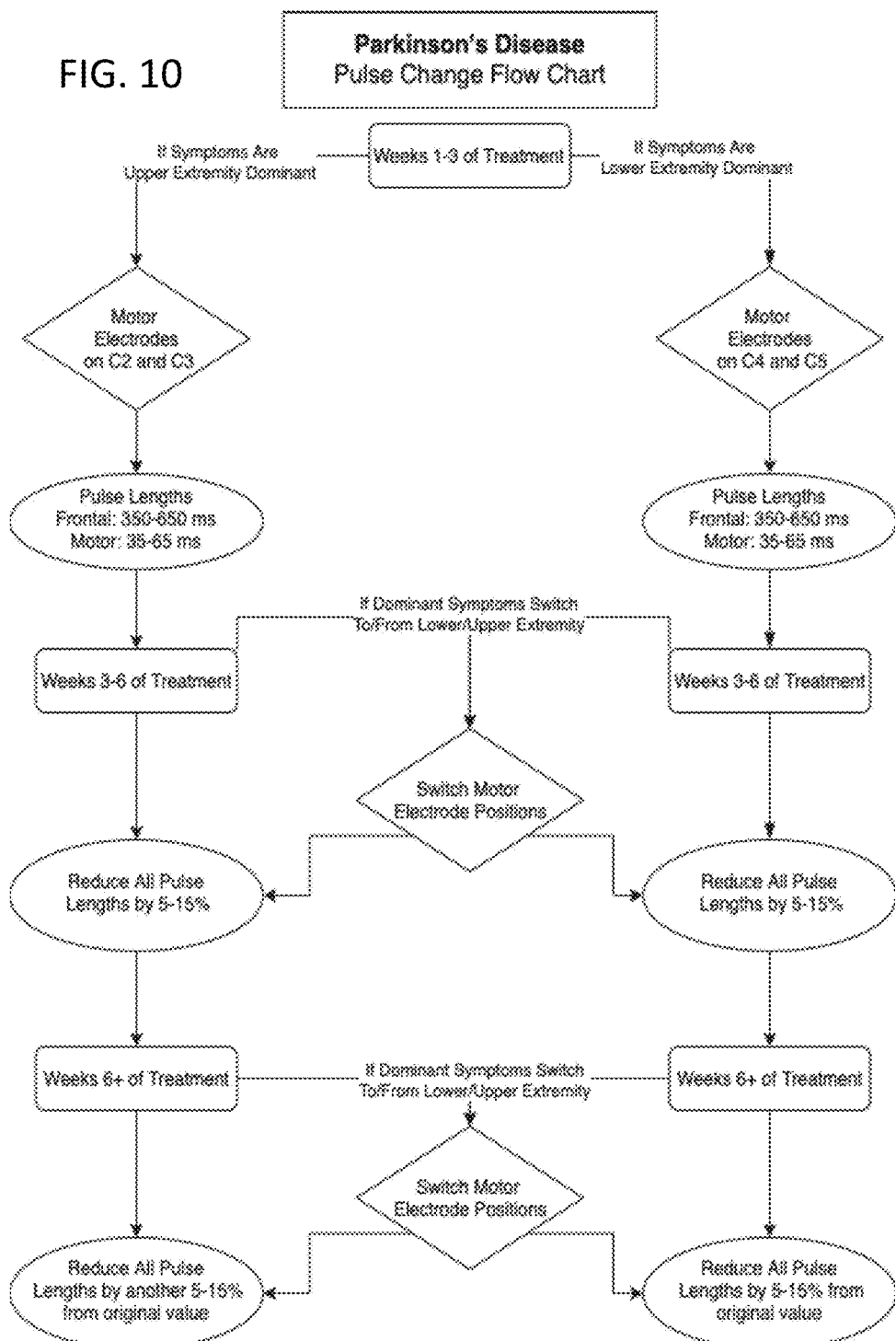
FIG. 10 is a flowchart of an exemplary treatment plan for Parkinson's disease for use with some embodiments.

In weeks 6+ of the stimulation treatment protocol specifically for Parkinson's disease, the 4 electrode positions on the scalp/skull/brain are modified if the symptoms in the Parkinson's disease patient shift from upper extremity dominant to lower extremity dominant or vice versa with electrodes changing between C2 or C3 to C4 or C5 respectively. In weeks 6+ of the stimulation treatment protocol, the pulse length, in the first 5 minutes of treatment, should reduce by another 5-15% (10-30% total shortening since weeks 1-3) calculated from the initial pulse length value chosen in weeks 1-3, in the next 15 minutes, to induce a higher voltage gradient value along the forceps minor than in weeks 1-6. A higher voltage gradient is helpful in weeks 6+ of the treatment to not let the brain reach a plateau of stimulation habituation and safely increase the amount of actions potentials sent downstream to the substantia nigra and subthalamic nucleus. In weeks 6+ of stimulation treatment protocol, the current magnitude may increase or stay constant depending on the clinical outcomes obtained from weeks 4-6 of treatment with current levels increasing if no changes in the Parkinson's disease patient symptomatology occurred in weeks 1-6. A qualified research technician and/or qualified healthcare worker should adjust parameters after measuring clinical outcomes obtained from weeks 1-3 and 4-6 of treatment through neuroimaging, psychometric/neurological assessments, and/or through neurological examination specific to Parkinson's disease. All other waveforms parameters including polarity switch frequency, interpulse break, and length of treatment stay constant. The total time of the stimulation treatment protocol in weeks 6+ still remains constant at 20 minutes where the first 5 minutes of stimulation is the frontal lobe and the next 15 minutes of stimulation is between the frontal lobe and motor cortex. Although the specific 6+ weeks stimulation treatment protocol regime is outlined in the last 3 paragraphs, pulses/waveforms in this paradigm can be tuned and ranged across different values specific pathophysiology of the patient suffering from Parkinson's disease. Pulses parameters that can be tuned and modulated are pulse length, interpulse break, polarity switch frequency, current magnitude, electrode positions, segment treatment time, and total treatment time. The specific stimulation treatment protocol for Parkinson's disease outlined above provides a base framework for pulse modulation over time that can be used with some embodiments. All treatments should occur before noon each day. A visual flowchart of pulse changing over time for the Parkinson's disease stimulation treatment protocol is presented in FIG. 10.

Furthermore, an invention and method can be specifically calibrated for the treatment of different classes of multiple sclerosis (progressive-primary, secondary-progressive, relapsing-remitting, and progressive-relapsing). The pathology of multiple sclerosis (M.S.) is characterized as large scale white matter atrophy in the cortex and spinal cortex leading to a wide range of symptoms both motor and non-motor. The tracts that have the greatest amount of correlation to symptoms in the M.S. Patients if demyelinated are the corticospinal tract and spanning fibers across the corpus callosum. tAPCS stimulations allow for greater subthreshold and suprathreshold stimulation to illicit initiation of action potentials across tracts in the cortex which leads to long term potential (myelination) to slow down and reverse disease progression in multiple sclerosis. The stimulation treatment protocol outlined below should run for a minimum of 12 weeks with the treatment being done for 20 minutes every day before noon. In weeks 1-6 of treatment, 6 electrodes are positioned on the scalp/skull/brain with two electrodes positioned on F3 and F4 and 4 hind electrodes are placed on the motor cortex based on the EEG 10-20 international system. The hind electrodes are positioned on the motor cortex with positions of C2, C3, C4, and C5. In weeks 1-6 of the stimulation treatment protocol, a 350-650 ms pulse length and 30-70 ms interpulse break with a polarity switch after every 4th 350-650 ms pulse occurs, 2-4 mA current pulse magnitude, and with current running back and forth between electrodes F3 and F4 for the first 5 minutes of treatment to induce sub-threshold tonic depolarizations of neurons with a low valued voltage gradient along the forceps minor. In the second 5 minute segment of the stimulation treatment protocol, a 350-650 ms pulse length, 30-70 ms interpulse break with no polarity switch, 2-4 mA current magnitude, between electrodes F4 and C3 occurs for 1-15 seconds, prior to switching contralaterally to run for 1-15 seconds between electrodes F3 and C2 with frontal electrodes are anode and hind motor cortex electrodes are cathode to induce a high value voltage gradient along the corticospinal tracts and the corpus callosum. The cathode and anode electrodes switch polarity every 40 seconds in the second 5 minute segment of treatment. In the third 5 minute segment of the stimulation treatment protocol, a 350-650 ms pulse length, 30-70 ms interpulse break with no polarity switch, 2-4 mA current magnitude, between electrodes F4 and C5 occurs for 10 seconds, prior to switching contralaterally to run for 1-15 seconds between electrodes F3 and C4 with frontal electrodes are anode and hind motor cortex electrodes are cathode. The cathode and anode electrodes switch polarity every 30-60 seconds in the third 5 minute segment of treatment. In the fourth 5 minutes segment of the stimulation treatment protocol, a 350-650 ms pulse length, 30-70 ms interpulse break with no polarity switch, 2-4 mA current magnitude, between electrodes F4 and C3+C5 occurs for 1-15 seconds, prior to switching contralaterally to run for 1-15 seconds between electrodes F3 and C2+C4 with frontal electrodes are anode and hind motor cortex electrodes are cathode. The cathode and anode electrodes do not switch polarity in the fourth 5 minute segment of stimulation treatment protocol. The total treatment time in the first 6 weeks of stimulation treatment protocol is 20 minutes with a 5 minute stimulation across the frontal cortex+forceps minor, and three separate 5 minute stimulation segments between frontal cortex and motor cortex across the corticospinal tract+corpus callosum.

Figure 11:
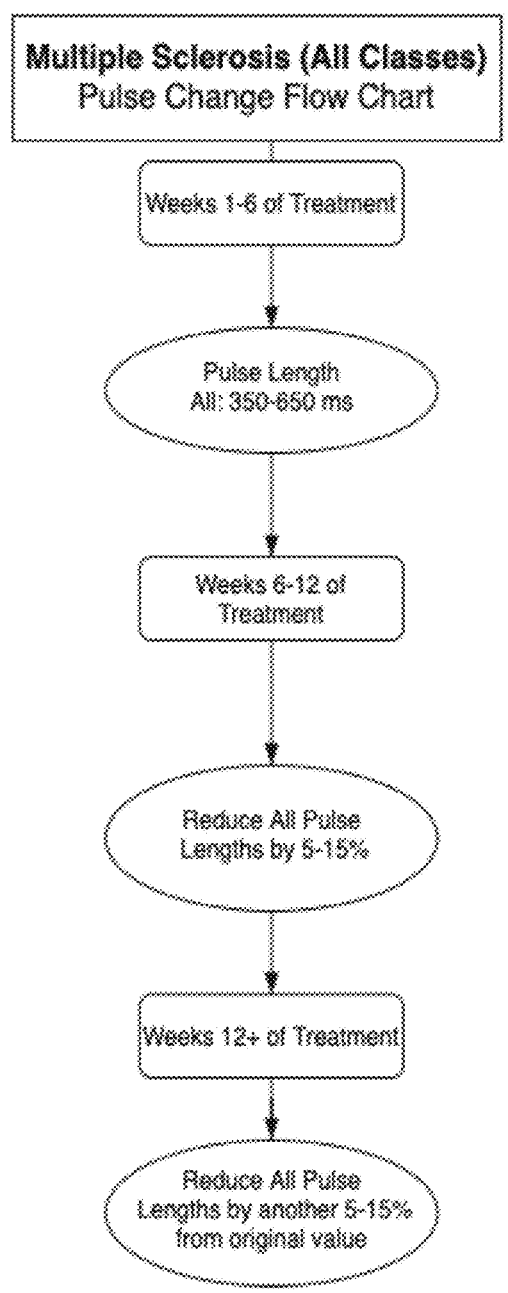
FIG. 11 is a flowchart of an exemplary treatment plan for multiple sclerosis for use with some embodiments.

In weeks 6-12 of the stimulation treatment protocol specifically for different classes of multiple sclerosis, the 6 electrode positions do not change relative to weeks 1-6. Furthermore, the pulse length in all 20 minutes of the stimulation treatment protocol should reduce by 5-15% from the initial pulse length value chosen in weeks 1-6 to increase the value of all the voltage gradients induced along the forceps minor, corticospinal tracts, and bundles stretching across the corpus callosum. Also, the stimulation treatment protocol, the current magnitude may increase or stay constant depending on the clinical outcomes obtained from weeks 1-6 of treatment with current levels increasing if no changes in the multiple sclerosis patient's symptomatology occurred in weeks 1-6. a qualified research technician and/or qualified healthcare worker should adjust parameters after measuring clinical outcomes obtained from weeks 1-6 of treatment through neuroimaging, psychometric/neurological assessments, and/or through neurological examination specific to multiple sclerosis. All other waveforms in weeks 6-12 of the stimulation treatment protocol including polarity switch frequency, interpulse break, and the length of treatment should stay constant. The total treatment time in the second 6 weeks of stimulation treatment protocol remains at 20 minutes with a 5 minute stimulation across the frontal cortex+forceps minor, and 3 separate 5 minute stimulation segments between frontal cortex and motor cortex across the corticospinal tract+corpus callosum. In weeks 12+ of the stimulation treatment protocol, the 6 electrode positions do not change relative to weeks 1-12. Furthermore, the pulse length in all 20 minutes of treatment, should reduce by another 15-30% (10-30% total shortening since weeks 1-3) which is calculated from the initial pulse length values chosen in weeks 1-3 ranging to further increase the value of all the voltage gradients to further induce a higher amount of depolarization and subsequent re-myelination across all tracts the voltage gradients lie across. The stimulation treatment protocol, the current magnitude may increase or stay constant depending on the clinical outcomes obtained from weeks 1-12 of treatment with current levels increasing if no changes in the multiple sclerosis patient's symptomatology occurred in weeks 1-12. A qualified research technician and/or qualified healthcare worker can adjust parameters after measuring clinical outcomes obtained from weeks 1-12 of treatment through neuroimaging, psychometric/neurological assessments, and/or through neurological examination specific to multiple sclerosis. All other waveforms parameters including polarity switch frequency, interpulse break, and length of treatment stay constant. The specific stimulation treatment protocol parameters for the pulses are specifically delineated above for the treatment of a majority of multiple sclerosis patients, more specific stimulation protocol treatment parameters for the pulses (pulse length, interpulse break, polarity switch frequency, current magnitude, electrode positions, segment treatment time, and total treatment time) can be tuned and ranged across different values to treat the specific pathophysiology of the patient. The optimized stimulation treatment protocol for multiple sclerosis is outlined above and provides a base framework of different pulse modulation over time that can be used with some embodiments. A visual flowchart of pulse changing over time for the multiple sclerosis stimulation treatment protocol is presented in FIG. 11.

Embodiments can be optimized to a stimulation protocol for dementia disorders. For dementia disorders, the stimulation treatment protocol is down twice a day with spacing of device-use being a minimum of 4 hours apart. The stimulation treatment protocol for dementia disorders should run for a minimum of 12 weeks. In weeks 1-6 of treatment, two electrodes are positioned on the scalp/skull/brain with the two electrodes positioned on F3 and F4. In the first 6 weeks of the stimulation treatment protocol that is specifically optimized for dementia and it's subtypes, a 0.1-10 ms (0.1-1 ms in some preferred embodiments) pulse length and 0.1-10 ms interpulse break with a polarity switch every 2-10 seconds, 2-4 mA current pulse magnitude, and with current running back and forth between electrodes F3 and F4 for all 20 minutes of treatment to induce supra-threshold depolarization of neurons with a high valued voltage gradient along the forceps minor. The cathode and anode electrodes switch polarity every 2-10 seconds in all 20 minutes of the stimulation treatment protocol to induce high fractional anisotropy along the forceps minor. The total treatment time in the first 6 weeks of stimulation treatment protocol is 20 minutes, twice a day, and spacing between sessions has to be at least 4 hours. To continue, in weeks 6-12 of the stimulation treatment protocol, the two electrode positions do not change relative to weeks 1-6 and the pulse length and inter-pulse spacing in all 20 minutes of the stimulation treatment session should stay the same. Furthermore, the polarity pulse switch time value should lower by 5-15% from the initial pulse switching time value to further increase alpha wave entrainment as measured by frontal cortex EEG electrodes. In weeks 6-12 of the stimulation treatment protocol, the current magnitude may increase or stay constant depending on the clinical outcomes obtained from weeks 1-6 of treatment with current levels increasing if no changes in the dementia symptomatology occurred in weeks 1-6. A qualified research technician and/or qualified healthcare worker should adjust parameters after measuring clinical outcomes obtained from weeks 1-6 of treatment through neuroimaging, psychometric/neurological assessments, and/or through neurological examination specific to the class of dementia being examined. All other waveform parameters stay the same and the treatment sessions are done twice a day for 20 minutes each session and with a spacing between sessions of at least 4 hours.

Figure 12:
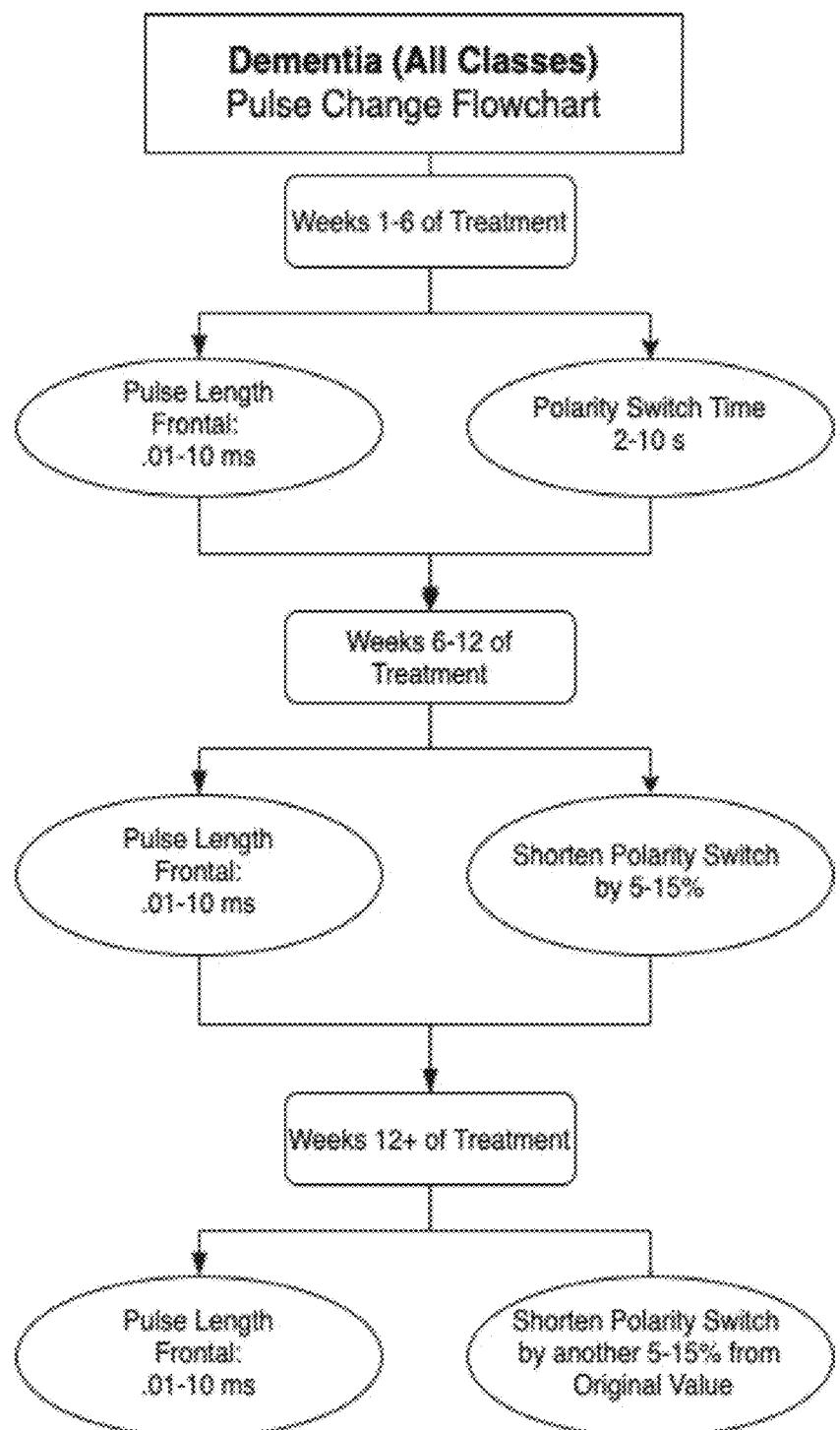
FIG. 12 is a flowchart of an exemplary treatment plan for dementia for use with some embodiments.

In weeks 12+ of the stimulation treatment protocol, the two electrode positions do not change. Also, the pulse length and inter-pulse spacing in all 20 minutes of the stimulation treatment session should stay the same as well. The polarity pulse switch time should have the polarity pulse switch value to lower by another 5-15% (10-30% total shortening since weeks 1-6) which is calculated from the initial polarity pulse switch time value in weeks 1-6 further increase alpha wave entrainment as measured by frontal cortex EEG electrodes. The polarity pulse switch time should not go lower than 1 second to not elicit any adverse events like migraines or headaches. The current magnitude may increase or stay constant depending on the clinical outcomes obtained from weeks 1-12 of treatment with current levels increasing if no changes in the dementia symptomatology occurred in weeks 1-12. A qualified research technician and/or qualified healthcare worker should adjust parameters after measuring clinical outcomes obtained from weeks 1-12 of treatment through neuroimaging, psychometric/neurological assessments, and/or through neurological examination specific to the class of dementia being examined. The specific stimulation treatment protocol parameters for the pulses are specifically delineated above for the treatment of a majority of dementia patients, more specific stimulation protocol treatment parameters for the pulses (pulse length, interpulse break, polarity switch frequency, current magnitude, electrode positions, segment treatment time, and total treatment time) can be tuned and ranged across different values to treat the specific pathophysiology for the patient. The specific stimulation treatment protocol for dementia is outlined above and provides a base framework of pulse modulation over time for use with some embodiments. A visual flowchart of pulse changing over time for the dementia stimulation treatment protocol is presented in FIG. 12.

Although certain embodiments of systems and methods for specific neuropsychiatric disorders and their classes (Parkinson's disease, multiple sclerosis, and dementia have been describe, embodiments be extended to non-medical, consumer applications for cognitive enhancement and consciousness modulation. In some embodiments, electrodes and sub-electrodes have a dual functioning property of being EEG electrodes and stimulation TCS electrodes. Embodiments include methods to combine many variables to create an advanced closed loop stimulation protocol using geography, weather, time-of-day, season, and EEG signals to modulate the pulse. These devices will have 4 electrodes with a 4×4 sub-electrodes array positioned around the frontal cortex and F3, F4, F7, and F8 which creates a 64 sub-electrode network across the frontal lobe. A machine learning/artificial-intelligence pipeline using recurrent neural networks can be constructed to predict EEG event-related states from these various variables. A wide range of algorithms will be constructed in the future whose conceptual basis is within this patent. Since this is a consumer device, current levels will be in the 0-2 mA to reduce, mitigate, and prevent adverse events. Furthermore, in the first week of device purchase, the device will be programmed to function as solely an EEG device to reduce, mitigate, and prevent adverse events. After 1 weeks, the stimulation across the frontal electrodes will be modulated on a biweekly basis to continually elicit plasticity in the user. Pulse/waveform modulation is dependent upon EEG recordings being collected from the electrode network across the frontal lobe. After the first week, the stimulation protocol will include stimulation breaks where the device will turn on its EEG functionality to record neural activity. There are many time ranges in which this can be done, where stimulation can occur for 10 minutes, then EEG recordings can occur for 5 minutes, and then stimulation is turned for the last 5 minutes. The most optimal protocol will be 30 seconds EEG recording, then a 9.5 minutes stimulation protocol, then a 30 Second EEG recording, then a 9.5 minutes stimulation protocol. However, many different variations of EEG to TCS time ranges can be conducted and experimented on with using embodiments. Electrode will not and cannot simultaneously record and stimulate the brain at a single moment in time. Furthermore, the device can be used for 20 minutes and at least a 4-16 hour period should elapse before the device is used again. The pulses will be modulated based on EEG, time of day, geography, weather of the day, and the current season being experienced by the user. For example, a faster pulse rate and/or higher current magnitude pulses occurs if the weather is cold, humid, and/or rainy which allows for a higher charge summation in the frontal cortex to induce higher state of consciousness in bad weather environments and/or low temperature seasons. Whereas, a slower pulse rate and/or lower current magnitude pulses occurs if the weather is hot, sunny, and/or spring-cool which allows for a smaller charge summation in the frontal cortex to modulate consciousness for warmer weather environments or high temperature seasons. As explained above, pulses, EEG recording, weather data, geographic information, time of day, and season are interlinked in an artificial intelligence pipeline to automate the pulse creation process in real time for users globally. Another example of modulating pulses based on geography, a faster pulse rate and/or higher current magnitude pulses occur for users in geographies with high altitudes to account for lowered blood oxygen levels to increase charge summation needed to substantially modulate spike trains in the frontal cortex. In contrast, a slower pulse rate and/or lower current magnitude pulses occur for users in geographies with lower altitude to account for higher blood oxygen levels as lower charge is used to substantially modulate spike trains in the frontal cortex. The pulse modulating algorithms will be updated in real time to increase the personalization and specifications of the pulses as more data is collected over time. This closed-loop protocol is not limited to the variables mentioned, in the future, variables collected from smart watches, ECG bands, neuroimaging data (MRI, CT, PET and/or MEG), diet/exercising tracking apps, and other devices/services that collect biometric data from an individual.

It should be noted that the specific pulses described above for Parkinson's disease, classes of multiple sclerosis, and classes of dementia are optimized to the specific parameters described. However, different parameters on the pulses can be chosen if a research technician specifies the need for new pulse parameters. Modifications to the current pulse protocols above may be implemented by those skilled in the art, without departing from the scope of the invention and method herein. It should also be noted that if embodiments of a treatment protocol are used alongside another treatment, specific considerations should take place before creating the waveforms. Other neuromodulation modalities include deep brain stimulation, transcranial magnetic stimulation, vagal nerve stimulation, and electroconvulsive therapy and that users that have a deep brain stimulation implant or undergoing electroconvulsive therapy are contraindications to using certain embodiments of pulse current waveforms in the device. Also, for TMS, the pulse waveform of some embodiments is dependent upon the pulse waveform of the TMS pulses being used if the patient is undergoing both treatments. If TMS pulse frequency is less than 5 Hz, the pulse length of some embodiments are less than 100 ms with a maximum 50 ms interpulse break to account for inhibitory TMS pulse stimulation. If TMS pulse frequency is between 5-20 Hz, the pulse length used in some embodiments will have a minimum 100 ms pulse length with a minimum 50 ms interpulse break to account for excitatory TMS pulse stimulation. As for vagal nerve stimulation, it is a contraindication to some embodiments if the vagal nerve stimulator is implanted. Noninvasive vagal nerve stimulators should have their pulse parameters collaborated by proper research technicians to optimize treatment performance while being used as a pulse waveform therapy device for migraine and/or cluster headache. Any device, therapy, treatment, and/or procedure should be used a minimum of 2 hours apart from some embodiments unless otherwise noted by a researcher or physician. All devices, therapies, treatments, and/or procedures should be approved or cleared for use by a regulatory oversight body (for example: FDA or EMA) before it can be used alongside some embodiments.

Electrode arrays can be arranged around the patient's brain (either directly or indirectly through layers of dura, skull, or skin). Furthermore, the electrodes and pulse sequence described herein may be arranged on any given region of the body to stimulate any biological tissue, including transcranial current stimulation in the brain. The embodiments, systems, and processes of the figures described herein are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention and method.

The invention claimed is:

1. A neurostimulation device comprising:
a plurality of electrodes configured to be placed around at least a portion of a patient head such that each electrode has a plurality of electrical paths through the brain of the patient to at least a subset of the other electrodes; and
a controller configured to selectively control current between sets of opposing electrodes through the patient brain to selectively stimulate a region of interest of the patient brain during a period of time that is less than a neuronal time integrity constant by
providing a first set of electrical current pulses to a first set of opposing electrodes to create a first electric field gradient across the patient brain, and
providing a plurality of additional sets of electrical current pulses to additional sets of opposing electrodes, each offset from the first set of electrodes, to create a plurality of non-uniform electric field gradients across the brain, each partially overlapping with the first electric field gradient, at least one non-uniform electric field gradient having an opposite polarity to the first electric field gradient,
wherein the non-uniform electric field gradients at least partially negate the first electric field gradient such that a first net potential is created in the region of interest in the patient brain that exceeds a predetermined neuron stimulation threshold and a second net potential is created in areas of the patient brain outside the region of interest that is less that the neuron stimulation threshold.

2. The neurostimulation device of claim 1, wherein the first net potential is a voltage gradient in the region of interest that does not exceed 10 mV/mm and a current through the patient's scalp provided by the electrodes does not exceed 4 mA.

3. The neurostimulation device of claim 1, wherein each electrode comprises an array of sub electrodes.

4. The neurostimulation device of claim 3, wherein the controller is further configured to selectively operate subsets of sub electrodes within the arrays to form the sets of opposing electrodes.

5. The neurostimulation device of claim 4, wherein the controller is further configured to repeatedly provide cycles of the first set and additional sets of electrical current pulses at a rate between 10 Hz to 100 kHz for a predetermined time.

6. The neurostimulation device of claim 5, wherein the controller is further configured to vary the subsets of sub electrodes selected during the predetermined time.

7. The neurostimulation device of claim 1, wherein the controller is further configured to utilize electrodes as EEG sensors.

8. The neurostimulation device of claim 7, wherein the controller is further configured to modify electrical pulse parameters of at least one of the first set and additional sets of electrical current pulses based on information gathered from the sensors.

9. A neurostimulation device comprising:
a plurality of electrodes configured to be placed around at least a portion of a patient head such that each electrode has a plurality of electrical paths through the brain of the patient to at least a subset of the other electrodes; and a controller configured to selectively control current between sets of opposing electrodes through the patient brain to selectively stimulate a region of interest of the patient brain during a period of time that is less than a neuronal time integrity constant by providing a first set of electrical current pulses across the region of interest using a first set of opposing electrodes to create a first electric field gradient across the patient brain, and providing a plurality of additional sets of electrical current pulses outside the region of interest using to additional sets of opposing electrodes, each offset from the first set of electrodes, to create a plurality of non-uniform electric field gradients across the brain, each partially overlapping with the first electric field gradient, at least one non-uniform electric field gradient having an opposite polarity to the first electric field gradient, wherein the non-uniform electric field gradients at least partially negate the first electric field gradient such that a first net potential exposed to the region of interest by the electrical currents exceeds a neuron stimulation threshold and a second net potential exposed to areas of the patient brain outside the region of interest is less that the neuron stimulation threshold.

10. The neurostimulation device of claim 9, wherein first net potential is a voltage gradient in the region of interest that does not exceed 10 mV/mm and a current through the patient's scalp provided by the electrodes does not exceed 4 mA.

11. The neurostimulation device of claim 9, wherein each electrode comprises an array of sub electrodes.

12. The neurostimulation device of claim 11, wherein the controller is further configured to selectively operate subsets of sub electrodes within the arrays to form the sets of opposing electrodes.

13. The neurostimulation device of claim 12, wherein the controller is further configured to repeatedly provide cycles of the first set and additional sets of electrical current pulses at a rate between 10 Hz to 100 kHz for a predetermined time.

14. The neurostimulation device of claim 9, wherein the controller is further configured to utilize electrodes as EEG sensors.

15. The neurostimulation device of claim 14, wherein the controller is further configured to modify electrical pulse parameters of at least one of the first set and additional sets of electrical current pulses based on information gathered from the sensors.

16. The neurostimulation device of claim 14, wherein the controller is further configured to vary the subsets of sub electrodes selected during the predetermined time.

17. A neurostimulation method for stimulating a region of a patient brain comprising steps of:

placing a plurality of electrodes around at least a portion of a patient head such that each electrode has a plurality of electrical paths through the brain of the patient to at least a subset of the other electrodes, wherein the electrodes are energized under control of a controller during a period of time that is less than a neuronal time integrity constant;

providing a first set of electrical current pulses to a first set of opposing electrodes to create a first electric field gradient across the patient brain; and providing a plurality of additional sets of electrical current pulses to additional sets of opposing electrodes, each offset from the first set of electrodes, to create a plurality of non-uniform electric field gradients across the brain, each partially overlapping with the first electric field gradient, at least one non-uniform electric field gradient having an opposite polarity to the first electric field gradient, wherein the controller selects the sets of electrical current pulses such that the non-uniform electric field gradients at least partially negate the first electric field gradient such that a first net potential exposed to the region of interest exceeds a predetermined neuron stimulation threshold and a second net potential exposed to areas of the patient brain outside the region of interest is less that the neuron stimulation threshold.

18. The method of claim 17, wherein first net potential is a voltage gradient in the region of interest that does not exceed 10 mV/mm and a current through the patient's scalp provided by the electrodes does not exceed 4 mA.

19. The method of claim 17, further comprising a step of monitoring the electrodes as EEG sensors by the controller.

20. The method of claim 17, further comprising a step of modifying electrical pulse parameters of at least one of the first set and the additional sets of electrical current pulses based on information gathered from the sensors.

* * * * *